US012737037B2

(12) United States Patent
Orihashi et al.

(10) Patent No.: US 12,737,037 B2
(45) Date of Patent: Sep. 15, 2026

(54) THERMAL SENSATION PRESENTATION APPARATUS AND THERMAL SENSATION PRESENTATION SYSTEM

(71) Applicant: Sony Group Corporation, Tokyo (JP)

(72) Inventors: Masaki Orihashi, Kanagawa (JP); Yuri Ishikawa, Kanagawa (JP); Yusuke Nakagawa, Kanagawa (JP); Yuhu Liu, Kanagawa (JP)

(73) Assignee: Sony Group Corporation, Tokyo (JP)

(*) Notice: Subject to any disclaimer, the term of this patent is extended or adjusted under 35 U.S.C. 154(b) by 0 days.

(21) Appl. No.: 18/854,410

(22) PCT Filed: Apr. 17, 2023

(86) PCT No.: PCT/JP2023/015277

§ 371 (c)(1),
(2) Date: Oct. 4, 2024

(87) PCT Pub. No.: WO2023/218863

PCT Pub. Date: Nov. 16, 2023

(65) Prior Publication Data

US 2025/0251780 A1 Aug. 7, 2025

(30) Foreign Application Priority Data

May 11, 2022 (JP) ................................ 2022-078405

(51) Int. Cl.
*G06F 3/01* (2006.01)
*A61M 21/00* (2006.01)

(52) U.S. Cl.
CPC ............ *G06F 3/011* (2013.01); *A61M 21/00* (2013.01); *G06F 3/016* (2013.01); *A61M 2021/0022* (2013.01); *A61M 2021/0066* (2013.01)

(58) Field of Classification Search
CPC .................................................. G06F 18/2178
See application file for complete search history.

(56) References Cited

U.S. PATENT DOCUMENTS

2008/0076679 A1* 3/2008 Shan ...................... C40B 50/18 506/40
2008/0268137 A1* 10/2008 Ikeda ..................... C23C 14/24 204/192.1

(Continued)

FOREIGN PATENT DOCUMENTS

| | | | | |
|---|---|---|---|---|
| JP | 09050232 | A | * | 2/1997 |
| JP | H09-050232 | A | | 2/1997 |
| JP | 2011-194023 | A | | 10/2011 |
| JP | 2020-135191 | A | | 8/2020 |

OTHER PUBLICATIONS

Search Report issued in International Patent Application No. PCT/JP2023/015277, mailed Jun. 13, 2023 and English translation of same. 5 pages.

(Continued)

*Primary Examiner* — Nan-Ying Yang
(74) *Attorney, Agent, or Firm* — XSENSUS LLP

(57) ABSTRACT

[Object] To provide a thermal sensation presentation apparatus and a thermal sensation presentation system that enable a user to present a thermal sensation at an appropriate timing.
[Solving Means] A thermal sensation presentation apparatus according to an embodiment of the present technology includes a measurement unit, a gas supply section, and a control unit. The measurement unit includes a warm/cool source, an enclosure, a movable section, and a control section. The enclosure has a space to accommodate the warm/cool source. The movable section moves heat generated by heating or cooling the warm/cool source to a predetermined temperature from the space to outside of the space. The control section generates a second control signal (Continued)

to heat or cool the warm/cool source to the predetermined temperature before generating a first control signal to drive the movable section.

20 Claims, 17 Drawing Sheets

(56) References Cited

U.S. PATENT DOCUMENTS

| | | | | |
|---|---|---|---|---|
| 2013/0188991 | A1* | 7/2013 | Kawata | G03G 15/2028<br>399/122 |
| 2021/0031451 | A1* | 2/2021 | Chimmalgi | B33Y 10/00 |
| 2021/0402869 | A1* | 12/2021 | Favela Tentori | B60L 58/26 |

OTHER PUBLICATIONS

Ito, Nobuteru, Ha Da, Hisakazu, "Arrangement and Evaluation of Heat Sources for Presenting Tactile Stimuli from Overall Surroundings in VR Space," ISPJ Entertainment Computing Symposium (EC2019).) Sep. 2019, p. 303-309,in particular section 4. 7 pages.
Yoshihide Saito and Yuichiro Kume, "A Feasibility_Study on Non-contact Thermal Display," [ online], vol. 39, No. 11, Mar. 10, 2015 [ May 30, 2023], p. 1-4, インターネット< < URL:https: //www. jstage. jst. go. jp/arti cle/itetr/39. 11/0/39.11_1/ article/-char/ ja>< DOI : 10.11485/itetr.39. 11.0 ⌋ > in particular section 1-3,7. 4 pages.

* cited by examiner (A)

(B)

(A)

(B)

(A)

(B)

(C)

(A)

(B)

(C)

(A)

(B)

(A)

(B)

(C)

(A)

(B)

(C)

(A)

(B)

(A)

(B)

(C)

(A)

(B)

(A)

(B)

THERMAL SENSATION PRESENTATION APPARATUS AND THERMAL SENSATION PRESENTATION SYSTEM

TECHNICAL FIELD

The present technology relates to a thermal sensation presentation apparatus and a thermal sensation presentation system for presenting a thermal sensation to a user.

BACKGROUND ART

One of tactile sensation stimuli is a warm/cool stimulus. For example, there is a known technique for presenting a thermal sensation to a user in conjunction with a moving image. For example, Patent Literature 1 describes that a warm/cool stimulator, which is a warm/cool source attached to the user, is controlled to be heated or cooled in advance at a predetermined timing so that a timing when a specific frame in the moving image is perceived by vision of the user and a timing when stimulation of a specific sense is perceived by a tactile sensation of the user are synchronized.

CITATION LIST

Patent Literature

Patent Literature 1: Japanese Patent Application Laid-open No. 2020-135191

DISCLOSURE OF INVENTION

Technical Problem

However, in Patent Literature 1, there are problems in that the user is insensitive to a temperature change because the warm/cool source is in contact with a presentation location (user's skin), and it is difficult to present the thermal sensation in accordance with a user's movement when no scenario, etc., is set in advance.

In view of the circumstances as described above, an object of the present technology is to provide a thermal sensation presentation apparatus and a thermal sensation presentation system that enable the user to present a thermal sensation at an appropriate timing.

Solution to Problem

The thermal sensation presentation apparatus according to an embodiment of the present technology includes a warm/cool source, an enclosure, a movable section, and a control section.

The enclosure has a space to accommodate the warm/cool source.

The movable section moves heat generated by heating or cooling the warm/cool source to a predetermined temperature from the space to outside of the space.

The control section generates a second control signal to heat or cool the warm/cool source to the predetermined temperature before generating a first control signal to drive the movable section.

The control section may generate the first control signal and the second control signal based on a scene condition.

The control section may generate the first control signal and the second control signal based on a position or a movement of the user in a real space or a virtual space.

The enclosure may have an opening surface that connects the space to the outside of the space.

The movable section is a shutter that can open and close the opening surface, and blocks the heat from moving out of the space in a closed state.

The movable section may be configured to support the warm/cool source and allow the warm/cool source to move toward the outside of the space.

The enclosure may have an opening surface that connects the space to the outside of the space.

The movable section is configured to allow the warm/cool source to move from the space to the outside of the space through the opening surface.

It may further include a tactile sensation presentation section that presents vibration or pressure.

The control section controls the tactile sensation presentation section when generating the first control signal.

The warm/cool source may be an infrared heater or a cooling fan.

The warm/cool source may be a resistance heater or a Peltier element.

It may further include a detection section that detects surroundings of the warm/cool source.

The control section generates the first control signal and the second control signal based on a detection result of the detection section.

The detection section may detect the position or the movement of the user who exists around the warm/cool source.

The control section generates the first control signal and the second control signal based on the position or the movement of the user.

A thermal sensation presentation system according to an embodiment of the present technology includes a generation section, a communication section, a warm/cool source, an enclosure, a movable section, and a control section.

The generation section generates information for presenting a thermal sensation to a user.

The communication section transmits the information generated by the generation section.

The enclosure has a space to accommodate the warm/cool source.

The movable section moves heat generated by heating or cooling the warm/cool source to a predetermined temperature from the space to outside of the space.

The control section acquires the information transmitted by the communication section and, based on the acquired information, generates a second control signal to heat or cool the warm/cool source to the predetermined temperature before generating a first control signal to drive the movable section.

MODE(S) FOR CARRYING OUT THE INVENTION

Figure 1:
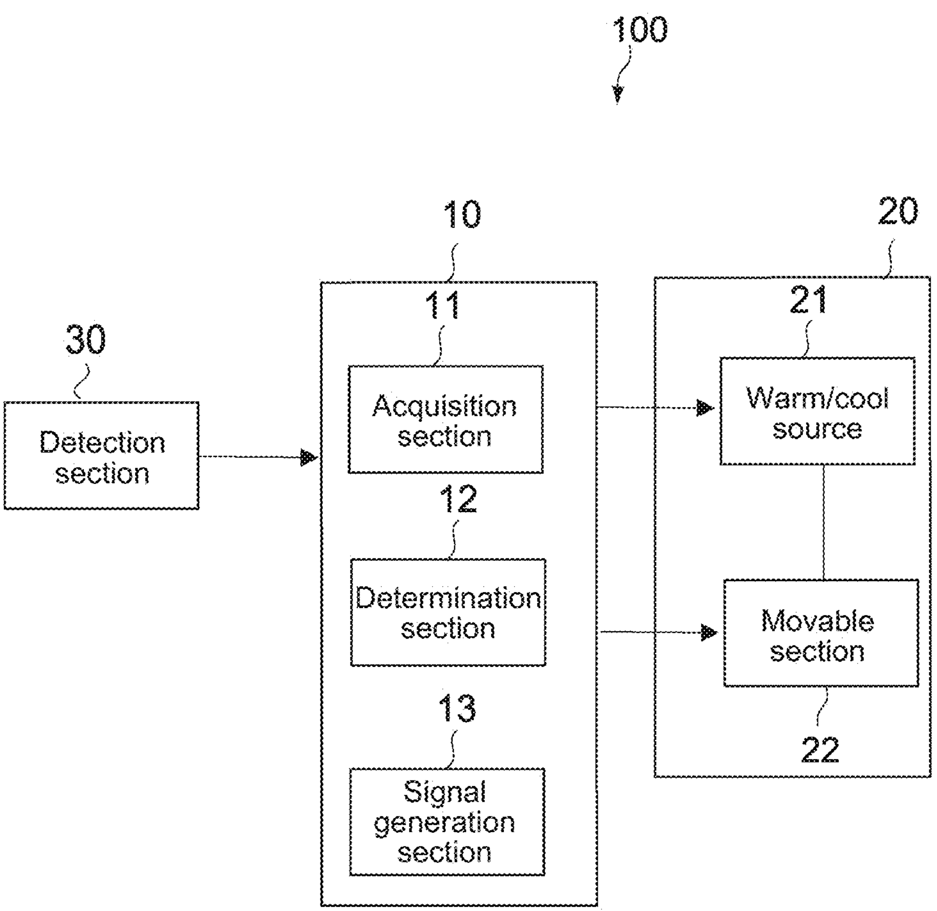
FIG. 1 A block diagram showing a configuration of a thermal sensation presentation apparatus in a first embodiment of the present technology.
Figure 2:
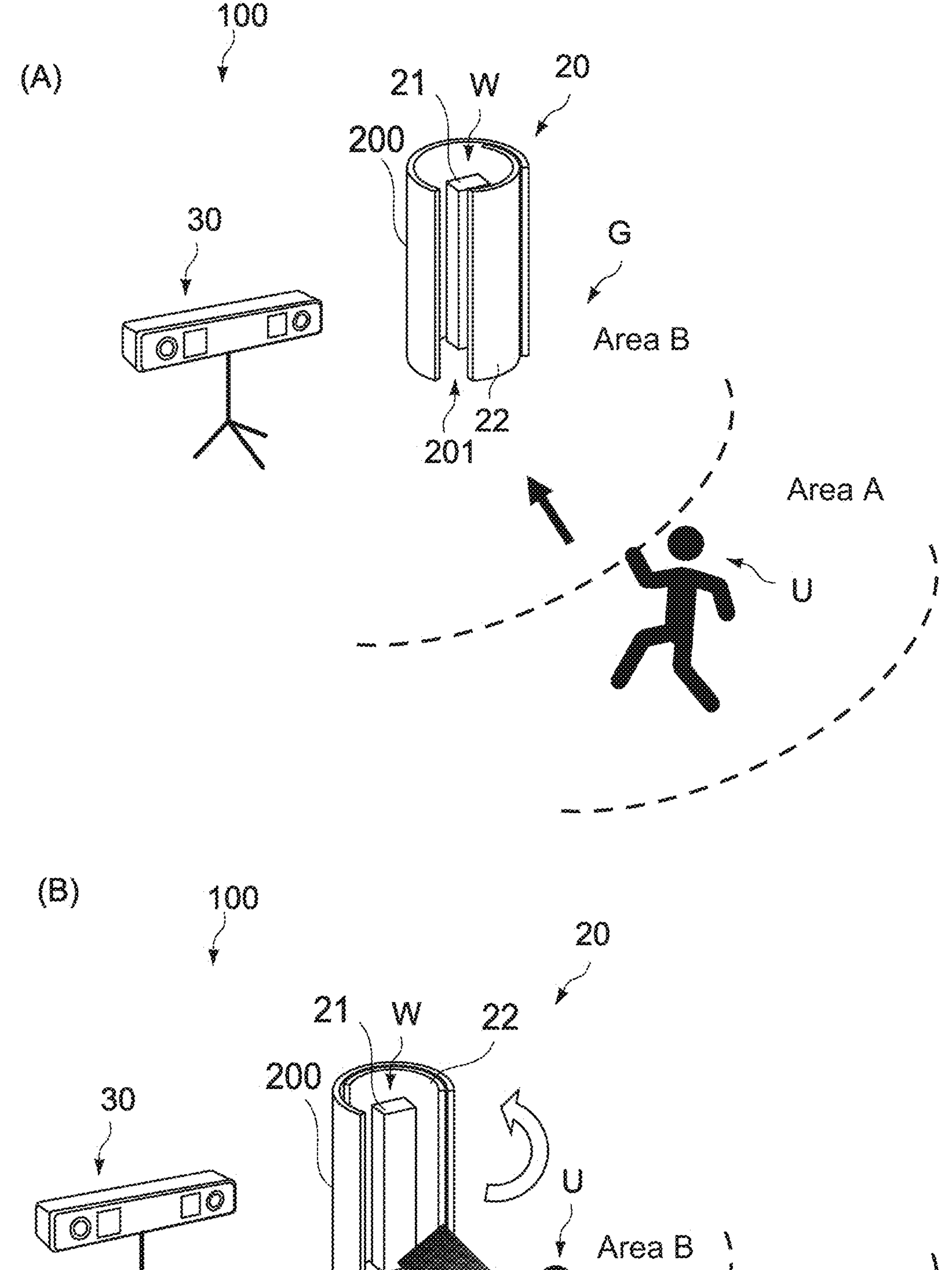
FIG. 2 A diagram showing an example of a use of the thermal sensation presentation apparatus, (A) shows that a user is about to enter an area B, and (B) shows that the user has entered the area B.
Figure 3:
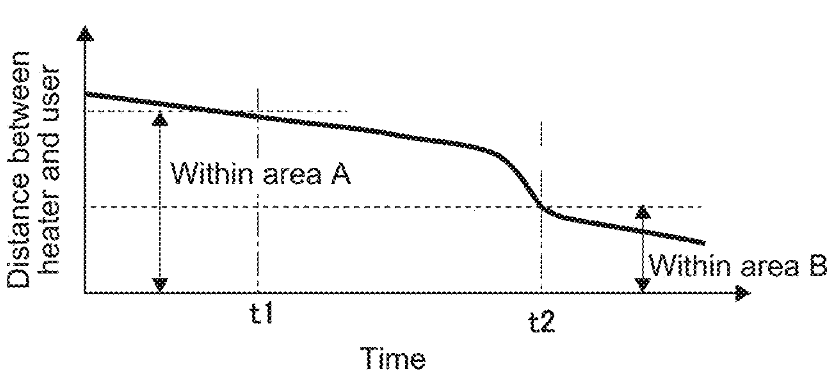
FIG. 3 A diagram showing a control of a heater, (A) shows a distance between the heater and the user, and (B) shows a temperature control of the heater.
Figure 3:
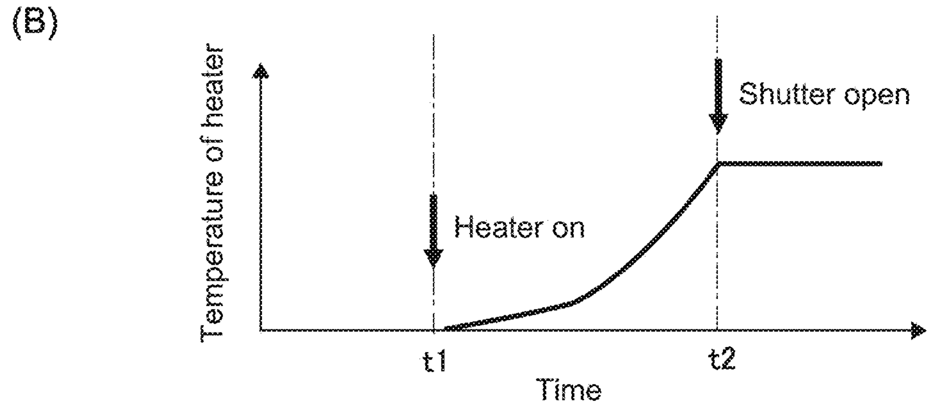

Embodiments of the present technology will be described below with reference to the drawings. FIG. 1 is a block diagram showing a configuration of a thermal sensation presentation apparatus 100 of this embodiment. FIG. 2 is a diagram showing an example of a use of the thermal sensation presentation apparatus 100, (A) shows that a user U is about to enter an area B, and (B) shows that the user U has entered the area B. FIG. 3 shows a control of a heater 21, (A) shows a distance between the heater 21 and the user U, and (B) shows a temperature control of the heater 21.

First Embodiment

[Thermal Sensation Presentation Apparatus]

As shown in FIG. 1, the thermal sensation presentation apparatus 100 has a control section 10, a warm/cool source unit 20, and a detection section 30.

(Warm/Cool Source Unit)

As shown in FIG. 2, the warm/cool source unit 20 has a warm/cool source 21, a movable section 22, and an enclosure 200. The warm/cool source 21 is installed on a floor surface G, has a rectangular parallelepiped shape parallel to a direction of gravity, and is capable of presenting a thermal sensation to the user U. Here, the floor surface G is a surface parallel to the surface on which the user U moves, for example, the ground. The thermal sensation is an alternative of a temperature sensation, and refers to a sensation with respect to temperature such as hotness (heat), warmth (warm), cool, and coldness.

In this embodiment, the warm/cool source 21 is a heat source, for example, an infrared heater, a hot air fan heater, or a stove (in this embodiment, warm/cool source 21 is called heater 21). In this embodiment, the heater 21 is installed on the floor surface G and has a semi-cylindrical shape parallel to the direction of gravity. However, it should be appreciated that it is not limited to this, and it may, for example, be hung in the enclosure 200, which is described below, or it may have a cylindrical shape.

The enclosure 200 has a cylindrical shape with an opening surface 201 that is installed on the floor surface G. The enclosure 200 has a space W that accommodates the heater 21. The opening surface 201 has an arc shape and a width of the opening surface 201 is wide enough to see one side of the warm/cool source 21 through the opening surface 201. The enclosure 200 is made of aluminum or stainless steel, for example.

In this embodiment, the enclosure 200 has the cylindrical shape installed on the floor surface G. However, it should be appreciated that it is not limited to this. For example, the enclosure 200 may be hanging from a ceiling, for example, or it may have a rectangular parallelepiped shape, and the opening surface 201 is not limited to the arc shape, but may also be flat.

The movable section 22 is a shutter that can open and close the opening surface 201 of the space W (in this embodiment, movable section 22 is called shutter 22). The shutter 22 has the arc shape and is configured to be capable of moving along the arc-shaped opening surface 201. The shutter 22 is opened and closed by the control section 10, which is described below. The shutter 22 is made of aluminum or stainless steel, for example.

In this embodiment, the shutter 22 has the arc shape, but it should be appreciated that it is not limited to this, and the shutter 22 may be flat.

(Detection Section)

The detection section 30 is installed on the floor surface G and detects a movement of the user U and a position of the user U. The detection section 30 detects within the areas (area A and area B), which are areas formed in predetermined ranges that include the warm/cool source unit 20 (see FIG. 2). The shape of the area detected by the detection section 30 is not especially limited, and can be, for example, oval, concentric, semi-circular or fan-shaped. The detection section 30 is, for example, an image detection apparatus such as a camera, a distance measurement detection apparatus such as a millimeter wave detection apparatus, or a LiDAR (Light Detection and Ranging) apparatus that combines the image detection apparatus and the distance measurement detection apparatus, or a magnetic motion tracker. The detection section 30 is configured to be capable of communicating with an acquisition section 11 described below, and can transmit detection information detected by the detection section 30 to the acquisition section 11. A communication means is wired or wireless (for example, Wi-Fi (registered trademark), LTE (Long Term Evolution), etc.), but is not especially limited to this.

In this embodiment, the detection section 30 is provided separately from the warm/cool source unit 20, but it should be appreciated that it is not limited to this, and the detection section 30 may be integrated with the warm/cool source unit 20.

(Control Section)

A control section 10 has the acquisition section 11, a determination section 12, and a signal generation section 13. The control section 10 is configured of a computer (information processing apparatus) including a CPU (Central Processing Unit) and a memory. The memory stores programs and various parameters to make the CPU perform various functions described below.

The acquisition section 11 acquires detection information from the detection section 30, and the determination section 12 determines an area in which the user U exists based on the detection information acquired by the acquisition section 11 in this embodiment. For example, in the case shown in (A) of FIG. 2, the determination section 12 determines that the user U exists in the area A. In the case shown in (B) of FIG. 2, the determination section 12 determines that the user U exists in the area B. If it is determined that the user U is outside of the area A or the user U is not detected by the detection section 30, the determination section 12 determines that the user U is outside of the area A.

The signal generation section 13 generates a first control signal to drive the shutter 22 and a second control signal to heat the heater 21 to a predetermined temperature (for example, 1100° C.). The signal generation section 13 generates the second control signal to heat the heater 21 to the predetermined temperature before generating the first control signal to drive the shutter 22 based on a determination result of the determination section 12. In other words, as shown in (A) and (B) of FIG. 3, the second control signal is generated when the user U enters the area A at time t1. Then, the first control signal is generated when the user U enters the area B at time t2.

[Operation of Thermal Sensation Presentation Apparatus]

An operation of the thermal sensation presentation apparatus 100 will be described. As a precondition, the thermal sensation presentation apparatus 100 is an apparatus that presents a thermal sensation to the user U when the user U enters the area B.

First, the detection section 30 detects which area the user U exists. Then, for example, if the user U exists outside of the area A, or if the user U is could not be detected, the determination section 12 determines that the user U is outside of the area A, and the signal generation section 13 does not generate the second control signal based on the determination result of the determination section 12 (state before time t1 in (A) and (B) of FIG. 3).

Next, if the determination section 12 determines that the user U exists in the area A based on a detection result of the detection section 30 as shown in (A) of FIG. 2, the signal generation section 13 generates the second control signal to heat the heater 21 to the predetermined temperature (state of time t1 to t2 in (A) and (B) of FIG. 3).

If the determination section 12 determines that the user U exists in the area B based on the detection result of the detection section 30 as shown in (B) of FIG. 2, the signal generation section 13 controls the shutter 22 to open (state after time t2 in (A) and (B) of FIG. 3).

This allows the thermal sensation presentation apparatus 100 to present a predetermined thermal sensation to the user U at a timing when the thermal sensation is presented to the user U (when user U enters area B in this embodiment). In other words, in this embodiment, the thermal sensation presentation apparatus 100 maintains the heater 21 heated to the predetermined temperature by the above timing. Therefore, it is possible to present the predetermined thermal sensation at the above timing, and a difference between the above timing and the thermal sensation perceived by the user U can be reduced.

Since the shutter 22 keeps the opening surface 201 closed until the above timing, it blocks heat generated by the warm/cool source 21 from being released outside of the space W. Here, blocking does not mean that the heat is not released completely, but rather means a function of the shutter 22 to prevent the heat from being released. When the shutter 22 is opened by the control section 10 at the above timing, the heat generated by heating the warm/cool source 21 to the predetermined temperature is transferred to a user U side. Therefore, the heat is transferred to the user U at once, and the user U can recognize the heat more easily.

In this embodiment, the warm/cool source 21 is the heater as a heat source, but it should be appreciated that it is not limited to this, and the warm/cool source 21 may also be a cooling fan, an air conditioner, or a cool air fan as a cool source.

In this embodiment, the control of the heater 21 is based on the distance between the user U and the warm/cool source 21, but it should be appreciated that it is not limited to this, and the control of the heater 21 may be based on the movement of the user U. For example, hot air may be generated when the user U makes a motion of swinging a sword down within a predetermined area. The detection section 30 may detect not only the human user U, but also the sword, for example. In that case, it may be controlled so that the hot air is generated as described above when that sword is swung down.

The control of the warm/cool source 21 is not limited to the above and may be controlled by time. For example, it may be controlled so that the heat is transferred to the user U when the user U stays in the predetermined area for a predetermined time, or it may be controlled so that the heat is transferred to the user U when the predetermined time has arrived in the predetermined area.

When the user U enters the area B before the warm/cool source 21 is heated or cooled to the predetermined temperature, the control section 10 may control the shutter 22 to open even if it is not heated or cooled to the predetermined temperature.

Modified Example 1-1

Figure 4:
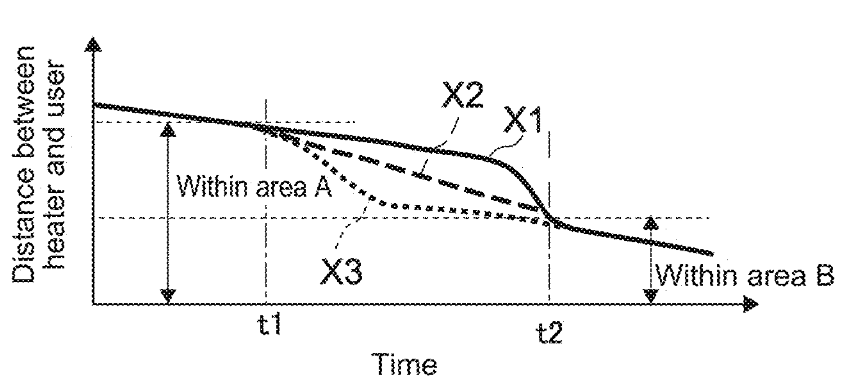
FIG. 4 A diagram showing a modified example of the control based on the distance between the heater and the user, (A) is a diagram showing the distance between the heater and the user, and (B) is a diagram showing the temperature control of the heater.
Figure 4:
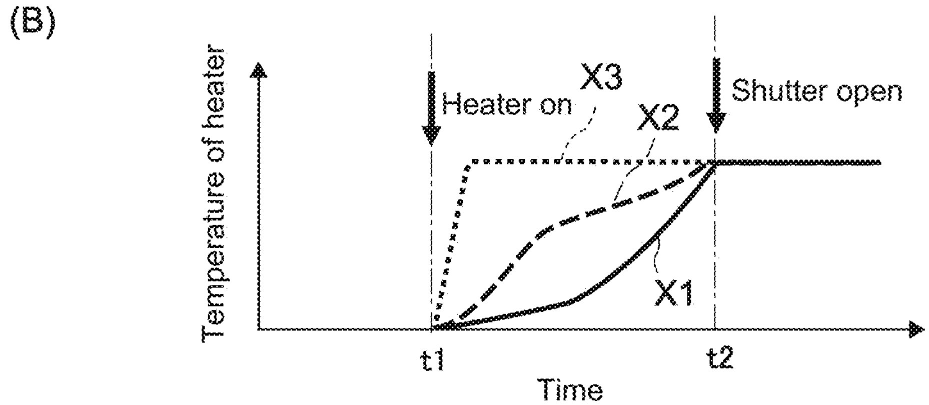

FIG. 4 is a diagram showing a modified example of the control based on the distance between the heater 21 and the user U in the first embodiment. (A) shows the distance between the heater 21 and the user U, and (B) shows the temperature control of the heater 21. Hereinafter, the configuration that differs from the first embodiment will be mainly described, and the configuration similar to the configuration of the first embodiment will be marked with the same symbols and its description will be omitted or simplified.

This modified example differs from the first embodiment in that the control section 10 controls an output of the heater 21 according to a speed of the user U in the area A. As shown in (A) of FIGS. 4, X1, X2, and X3 indicate the speed at which the user U approaches the heater 21. With respect to the X1, the speed increases around time t2 and it enters the area B. With respect to the X2, it enters the area B at an almost constant speed. With respect to the X3, the speed increases immediately after entering the area A and then entering the area B at a slow speed.

X1 to X3 in (B) of FIG. 4 correspond to the X1 to the X3 in (A) of FIG. 4. In the case of the X1 in (A) of FIG. 4, as the speed of the user U increases around t2, the temperature of the heater 21 rises in conjunction therewith. In the case of the X2, as the speed is almost constant after entering the area A, the temperature of the heater 21 rises at an almost constant interval. In the case of X3, as the speed is increased rapidly after entering the area A, the temperature of the heater 21 also rises rapidly from t1.

This allows the predetermined thermal sensation to be presented to the user U at an appropriate timing. In this modified example, the warm/cool source 21 is the heater, but it is not limited to this, and may be a cool source such as the cool air fan.

Modified Example 1-2

Figure 5:
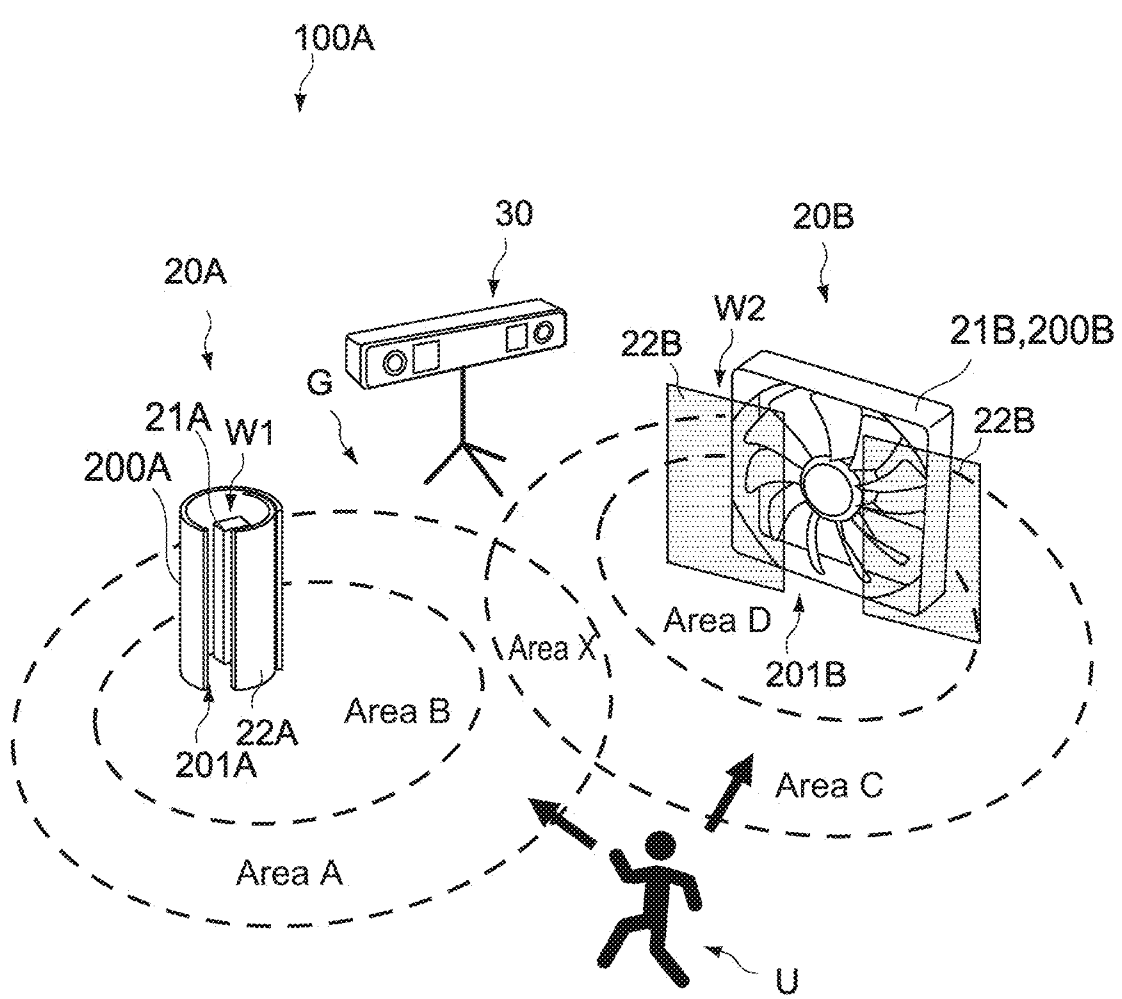
FIG. 5 A diagram showing a modified example of a thermal sensation presentation apparatus.
Figure 6:
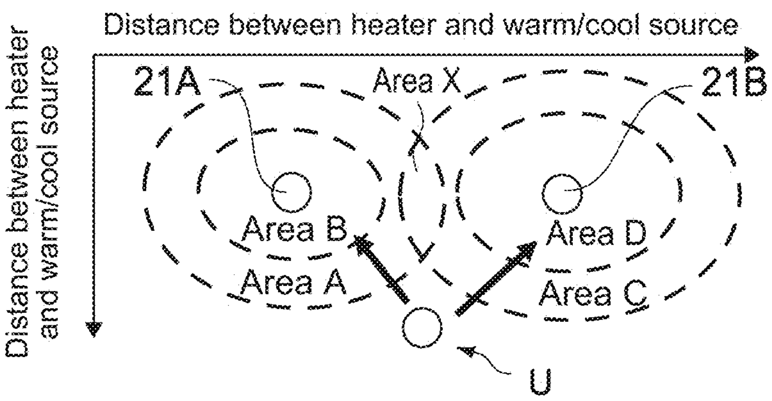
FIG. 6 A diagram showing a control of the heater, (A) shows a distance between the heater and the user and a distance between a cool air fan and the user, (B) shows a temperature control of the heater, and (C) shows a rotation speed control of the cool air fan.
Figure 6:
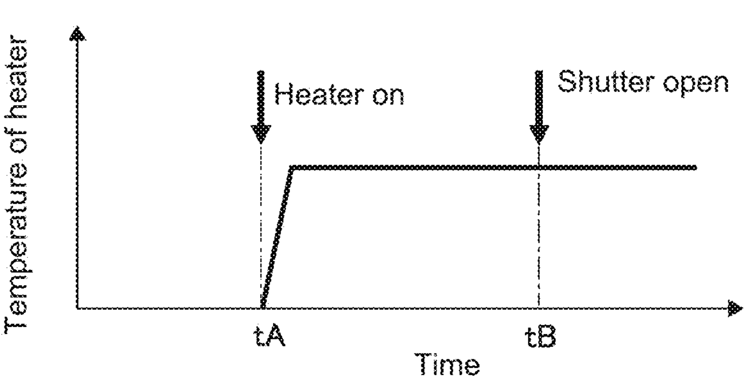
Figure 6:
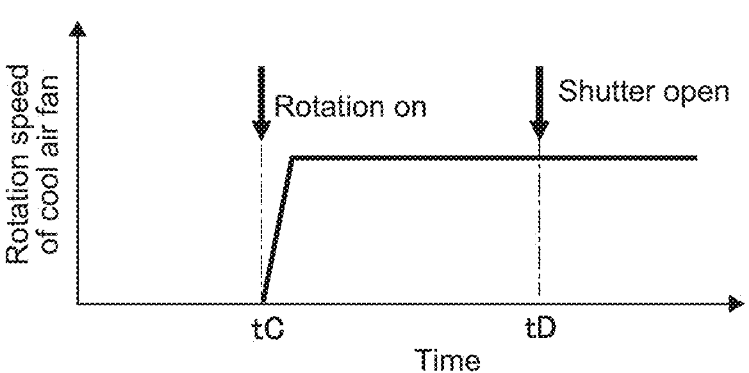

FIG. 5 is a diagram showing an example of a use of a thermal sensation presentation apparatus 100A in the modified example 1-1 of the first embodiment. FIG. 6 shows a control of a heater 21A and a cool air fan 21B. (A) shows a distance between the heater 21A and the user U and a distance between the cool air fan 21B and the user U, (B) shows the temperature control of the heater 21A, and (C) shows a rotation speed control of the cool air fan 21B. Hereinafter, the configuration that differs from the first embodiment will be mainly described, and the configuration similar to the configuration of the first embodiment will be marked with the same symbols and its description will be omitted or simplified.

This modified example differs from the first embodiment in that two warm/cool source units 21 are provided. In this modified example, the warm/cool source unit 20 has a heat source unit 20A and a cool source unit 20B.

The heat source unit 20A, as in the first embodiment, has the heater 21A, an enclosure 200A having a space W1 that accommodates the heater 21A, and a shutter 22A that is the movable section 22 that can open and close an opening surface 201A of the enclosure 200A. The cool source unit 20B has a cool air fan 21B, a shutter 22B is the movable section 22 that can open and close an opening surface 201B that is a front surface of the cool air fan 21B, and an enclosure 200B that accommodates the cool air fan 21 through the shutter 22B and a predetermined space W2.

The cool air fan 21B is a cool source that is installed on the floor surface G and has rotating blades. The cool air fan 21B can transmit cool air to the user U by rotating the rotating blades. The cool air fan 21B may have a fixed or variable (swiveling) direction of airflow. It should be appreciated that it is not limited to the cool air fan and it may be a cooling fan, an air conditioner, etc. In this embodiment, the cool air fan 21B is installed on the floor surface G. However, it should be appreciated that it is not limited to this, and, for example, it may be hung from the enclosure 200B described below.

The enclosure 200B has an opening surface 201B installed on the floor surface G and accommodates the cool air fan 21. The space W may have enough area to allow cool air to escape to both sides of the space W when the cool air fan 21B operates with the shutter 22B closed, as described below. The opening surface 201B has a flat shape, and a width of the opening surface 201B is enough to see the entire rotating blades of the cool air fan 21B.

In this embodiment, the enclosure 200B is a rectangular parallelepiped shape installed on the floor surface G. However, it should be appreciated that it is not limited to this. For example, the enclosure 200B may be hung from the ceiling, for example, and the opening surface 201B is not limited to the flat shape, but may also have the arc shape.

The movable section 22B is a shutter that can open and close the opening surface 201B of the space W2 (movable section 22B is called shutter 22B in this modification). The shutter 22B has the flat shape and is configured to be capable of moving along the flat-shaped opening surface 201B. The shutter 22B is opened and closed by the control section 10.

In this embodiment, the shutter 22B has the flat shape, but it should be appreciated that it is not limited to this, and the shutter 22B may have an arc shape.

(Detection Section)

The detection section 30 is installed on the floor surface G to detect the movement of the user U and the position of the user U. The detection section 30 detects within the areas (area A and area B), which are the areas formed in the predetermined ranges that include the warm/cool source units 20 (heat source unit 20A and cool source unit 20B) (see FIG. 5). The shape of the area detected by the detection section 30 is not limited, and can be, for example, oval, concentric, semi-circular or fan-shaped.

In this embodiment, the detection section 30 is installed separately from the warm/cool source unit 20, but it should be appreciated that it is not limited to this, and the detection section 30 may be installed in the warm/cool source unit 20.

(Control Section)

The determination section 12 determines with respect to areas A, B, C, and D as in the first embodiment. With respect to the area X, if the user U enters into the area X, the determination section 12 determines that the user U exists in the area X. Here, the area X is an area where the area A overlaps the area B.

The signal generation section 13 generates the first control signal to drive one or both of the shutters 22A and 22B, or the second control signal to drive one or both of the heater 21A and the cool air fan 21B. The signal generation section 13 generates the second control signal before generating the first control signal based on the determination result of the determination section 12. In other words, as shown in (A), (B) and (C) of FIG. 6, the second control signal is generated when the user U enters into the area A or the area C at time tA or time tC. Then, the first control signal is generated when the user U enters into the area B or the area D at time tB or time tD.

Here, the case in which the user U enters into the area X will be described. If the determination section 12 determines that the user U exists in the area X, the signal generation section 13 generates the second control signal to drive both the heater 21A and the cool air fan 21B.

[Operation of Thermal Sensation Presentation Apparatus]

An operation of the thermal sensation presentation apparatus 100A will be described. The thermal sensation presentation apparatus 100A is an apparatus that presents the thermal sensation to the user U when the user U enters the area B or the area D.

First, the detection section 30 detects which area the user U exists. Then, for example, if the user U exists outside of the area A and the area C or if the user U is not detected, the determination section 12 determines that the user U is outside of the area A and the area C, and the signal generation section 13 does not generate the second control signal based on the determination result of the determination section 12 (state before time tA in (B) of FIG. 6 and time tC in (C) of FIG. 6).

Next, if the determination section 12 determines that the user U exists in the area A based on the detection result of the detection section 30, the signal generation section 13 generates the second control signal to heat the heater 21A to the predetermined temperature (state of time tA to tB in (B) of FIG. 6). If the determination section 12 determines that the user U exists in the area C, the signal generation section 13 generates the second control signal to rotate the cool air fan 21B at a predetermined rotation speed (state of time tC to tD in (C) of FIG. 6). If the determination section 12 determines that the user U exists in the area X, the signal generation section 13 generates the second control signal to drive the heater 21A and the cool air fan 21B.

If the determination section 12 determines that the user U exists in the area B based on the detection result of the detection section 30 as shown in (B) of FIG. 6, the signal generation section 13 controls the shutter 22A to open (state after time tB in (B) of FIG. 6). If the determination section 12 determines that the user U exists in the area D, the signal generation section 13 controls the shutter 22B to open (state after time tC in (C) of FIG. 6).

This allows the thermal sensation presentation apparatus 100 to present the predetermined thermal sensation to the user U at the timing when the thermal sensation is presented to the user U (in this embodiment, when user U enters area B or area D). In other words, in this modified example, the thermal sensation presentation apparatus 100 creates a state in which the heater 21A is heated to the predetermined temperature or the cool air fan 21B is rotated at the predetermined rotation speed by the above timing. This makes it possible to present the predetermined thermal sensation at the above timing, thereby reducing a difference between the above timing and the thermal sensation perceived by the user U.

With respect to the shutter 22B, since the opening surface 201B is closed until the above timing, it guards the cool air from being released outside of the space W. When the opening surface 201B is closed and the cool air fan 21B is driven, cool air escapes from both sides of the space W2, thus preventing the cool air from hitting the user U before the shutter 22B is opened. At the above timing, not only the heat described above in the first embodiment but also the cool air generated by the cool air fan 21B, which is rotated at the predetermined rotational speed, can move to the user U side. Therefore, the cool air is transmitted to the user U at once, and the user U can more easily recognize the thermal sensation.

In this modified example, the heat source unit 20A and the cool source unit 20B are provided, thereby being capable of presenting various thermal sensations to the user U.

In this modified example, if the user U exists in the area X, the signal generation section 13 drives the heater 21A and the cool air fan 21B so that the user U can enter either the area B or the area D. Thus, if the user U enters the area B or the area D, it is possible to present the predetermined thermal sensation to the user U at the appropriate time.

In this modified example, the warm/cool source 21 includes the heater 21A and the cool air fan 21B, but it should be appreciated that it is not limited to this, and there may be two heaters. Also, the number of warm/cool source 21 is not limited to two, but may be three or more.

In this modified example, the area X is formed, but it is not necessarily formed when there are two or more warm/cool sources 21. In other words, the area X may not be formed depending on a distance between the warm/cool sources 21 or a size of the area.

Modified Example 1-3

Figure 7:
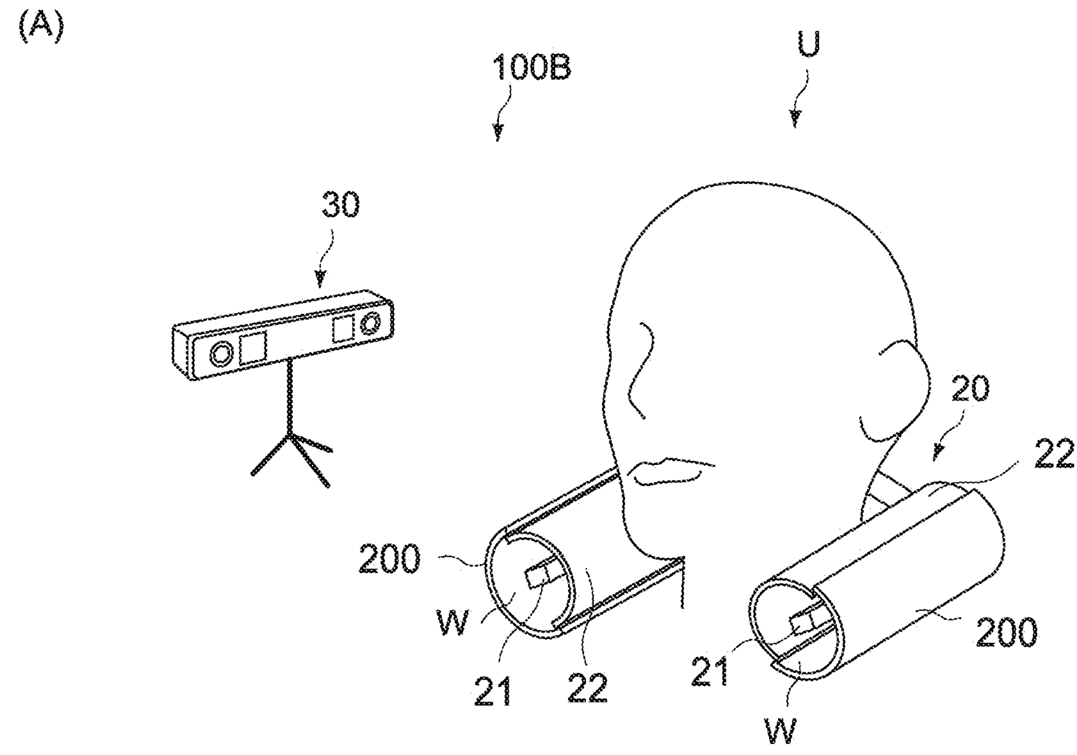
FIG. 7 A diagram showing an example of a use of a thermal sensation presentation apparatus in modified example 1-2 of the first embodiment, (A) shows a state in which the shutter is closed, and (B) shows a state in which the shutter is opened.
Figure 7:
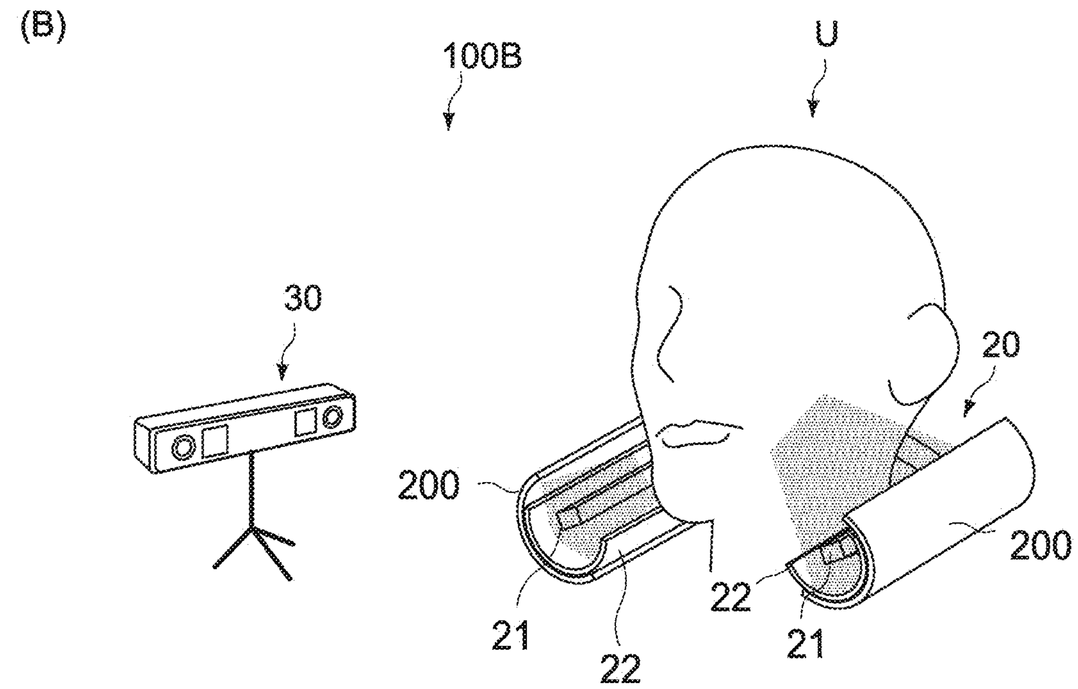

FIG. 7 is a diagram showing an example of a use of a thermal sensation presentation apparatus 100B in modified example 1-3 of the first embodiment, (A) shows a state in which the shutter 22C is closed, and (B) shows a state in which the shutter 22C is opened. Hereinafter, the configuration that differs from the first embodiment will be mainly described, and the configuration similar to the configuration of the first embodiment will be marked with the same symbols and its description will be omitted or simplified.

This modified example differs from the first embodiment in that the thermal sensation presentation apparatus 100B is wrapped around a neck of the user U. In this modified example, the warm/cool source 21 is a heater, but it should be appreciated that it is not limited to this, and the warm/cool source 21 may be a cooling fan or the like. The description of the warm/cool source unit 20 is similar to the first embodiment and is therefore omitted.

An operation of the thermal sensation presentation apparatus 100B is similar to that of the first embodiment, and therefore, the description will be omitted. Unlike the first embodiment, in this modified example, the warm/cool source unit 20 is wrapped around the neck, so that heat generated by being heated to the predetermined temperature (for example, 200° C.) by the heater 21 can be transmitted from the space W to the face of the user U ((A), (B) of FIG. 7). This allows the predetermined thermal sensation to be presented to a specific part of the user U. In this modified example, the warm/cool source unit 20 is wrapped around the neck, but it should be appreciated that it is not limited to this, and the warm/cool source unit 20 may be wrapped around an ankle, a wrist, a torso, a head, etc.

Second Embodiment

Figure 8:
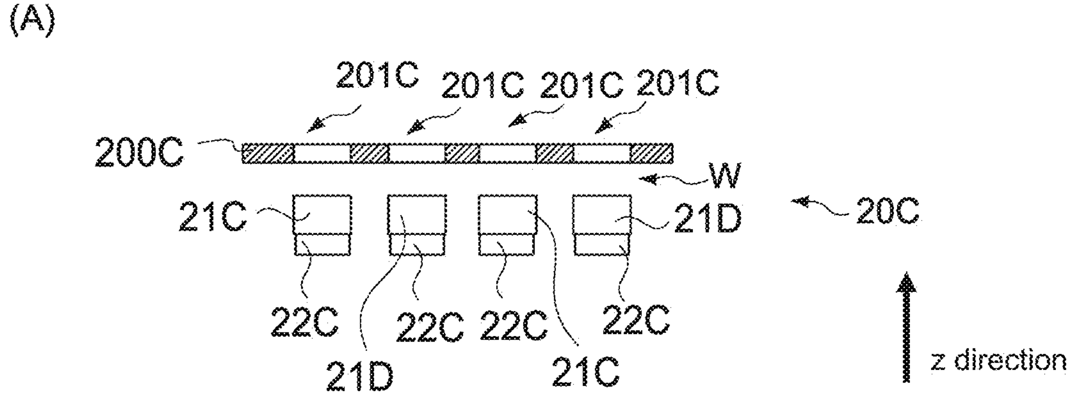
FIG. 8 A diagram showing an example of a use of a warm/cool source unit of a thermal sensation presentation apparatus in a second embodiment of the present technology, (A) shows that no thermal sensation presentation is performed, (A) shows that the thermal sensation presentation is performed by a heat source, and (B) shows that the thermal sensation presentation is performed by a cool source.
Figure 8:
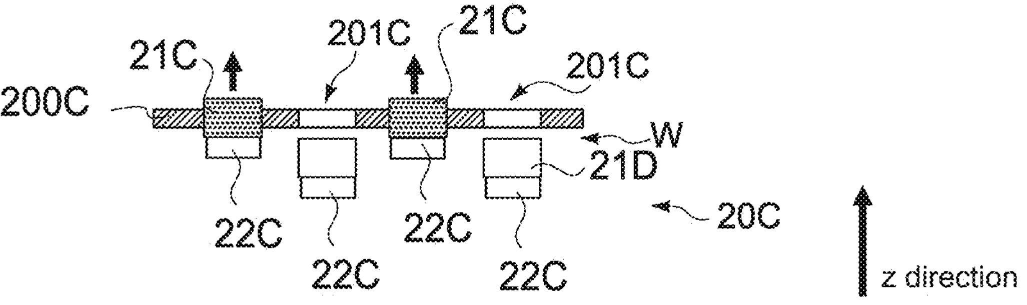
Figure 8:
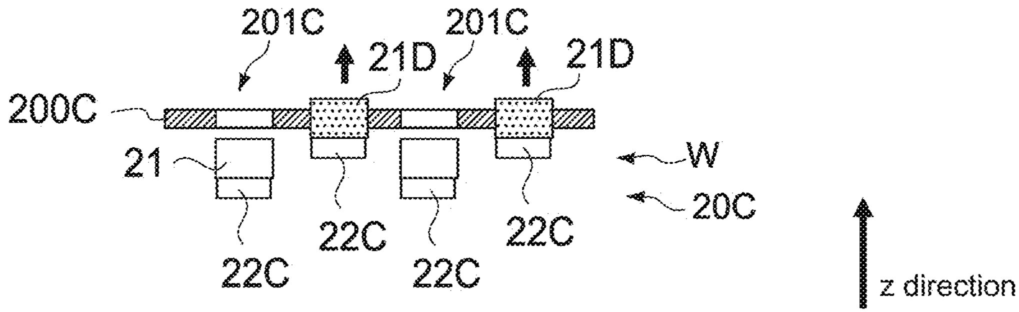
Figure 9:
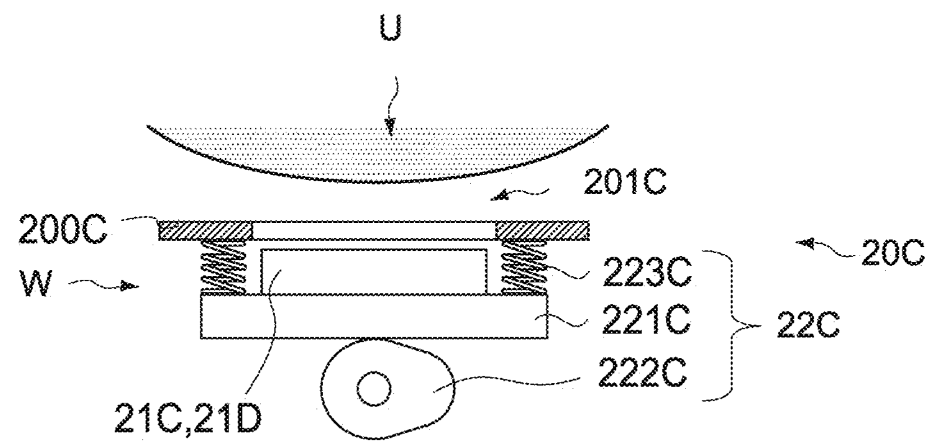
FIG. 9 A configuration of a movable section of the second embodiment, (A) shows before driving, and (B) shows during driving.
Figure 9:
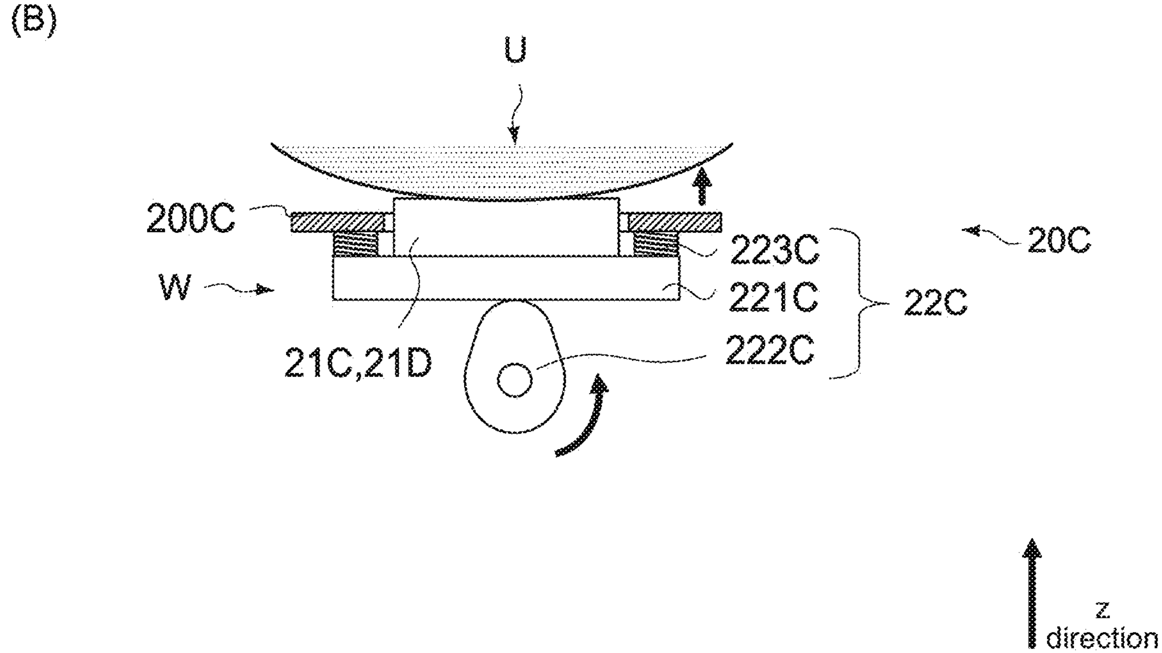

FIG. 8 is a diagram showing an example of a use of a warm/cool source unit 20C of the thermal sensation presentation apparatus in a second embodiment of the present technology, (A) shows that no thermal sensation presentation is performed, (B) shows that the thermal sensation presentation is performed by a heat source 21C, and (C) shows that the thermal sensation presentation is performed by a cool source 21D. FIG. 9 shows a configuration of a movable section 22C. (A) shows the movable section 22C before driving and (B) shows the movable section 22C during driving. Hereinafter, the configuration that differs from the first embodiment will be mainly described, and the configuration similar to the configuration of the first embodiment will be marked with the same symbols and its description will be omitted or simplified.

This embodiment differs from the first embodiment in that the heat generated by the thermal sensation presentation apparatus 100C is brought into contact with the user U. As shown in (A) of FIG. 8, the warm/cool source unit 20C has Peltier elements 21C for heating and Peltier elements 21D for cooling, which are the heat/cool sources, the movable section 22, and the enclosure 200C.

The Peltier elements 21C and 21D are electrical heat converters that generate a temperature difference when an electric current passes through them based on the Peltier effect, enabling the temperature control such as cooling or heating by changing a direction and magnitude of the current. The Peltier elements 21C and 21D are configured to be capable of presenting the thermal sensation when in contact with the user U. Sizes of the Peltier elements 21C and 21D are not especially limited, but they are square-shaped, for example, with 3 mm on a side.

The enclosure 200C is provided on a wrist of the user U, for example, and has opening surfaces 201C. The enclosure 200 has a space W that accommodates the Peltier elements 21C, 21D. The opening surfaces 201C may be large enough to allow the Peltier elements 21C, 22D to enter and exit, for example, is square-shaped, and has roughly 4 mm on a side.

The movable sections 22C are configured to allow the Peltier elements 21C, 21D to move from the space W to outside (user U side) of the opening surfaces 201C, which is a positive direction of the Z axis. As shown in (A) and (B) of FIG. 9, the movable section 22C is a cam mechanism having a support plate 221C supporting the Peltier elements 21C, 22D, a rotary plate cam 222C configured to allow the support plate 221C to move between the user U side and the space W, and a spring part 223C provided between the support plate 221C and the enclosure 200C.

The movable section 22C allows the Peltier elements 21C and 21D supported by the support plate 221C to reciprocate in the Z-axis direction by rotating the rotary plate cam 222C, which has an eccentric center of gravity. Since the spring part 223C allows the support plate 221C to press against the rotary plate cam 222C, the support plate 221C can be moved along a movement of the rotary plate cam 222C.

Figure 10:
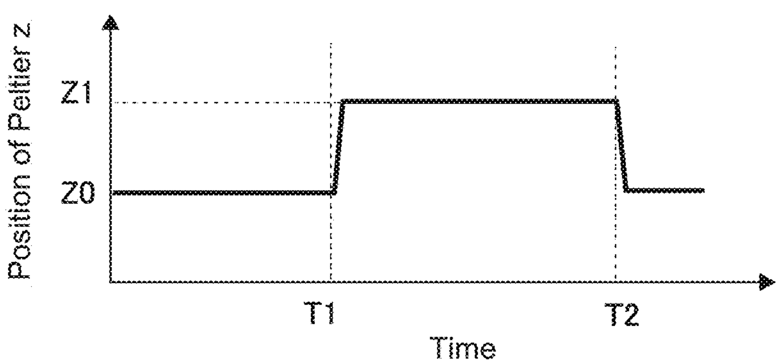
FIG. 10 A diagram showing a temperature control of Peltier elements based on a position of the Peltier elements, (A) shows the position of the Peltier elements, (B) shows the temperature control of the Peltier element for heating, and (C) shows the temperature control of the Peltier element for cooling.
Figure 10:
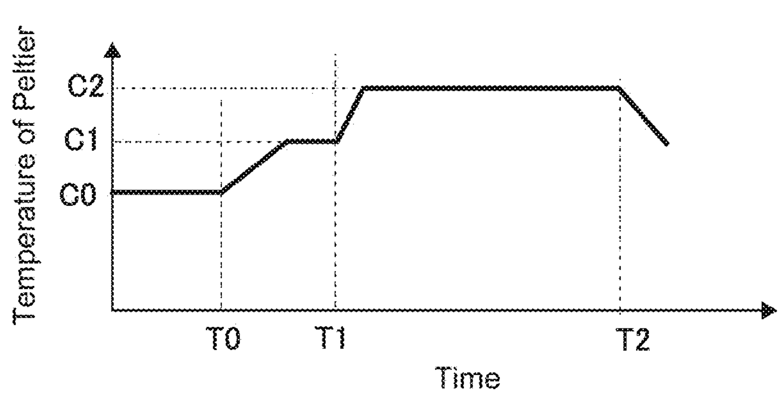
Figure 10:
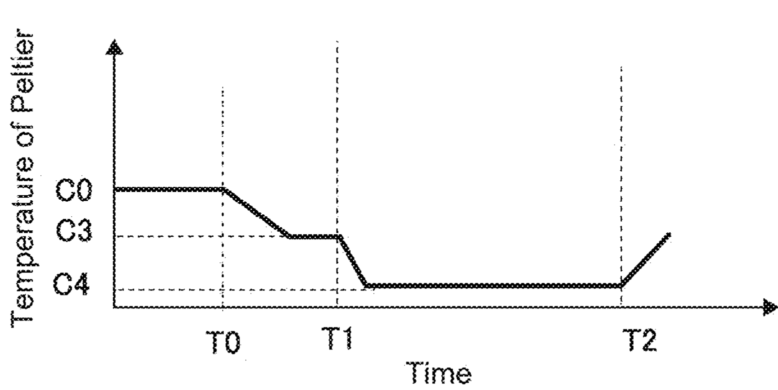

FIG. 10 is a diagram showing the temperature control of the Peltier elements 21C and 22D based on the position of the Peltier elements 21C and 22D. (A) shows the position of the Peltier elements 21C and 21D, (B) shows the temperature control of the Peltier element 21C for heating, and (C) shows the temperature control of the Peltier element 21D for cooling.

As shown in (A) of FIG. 10, the movable section 22C raises the position of the Peltier elements 21C and 21D from Z0 to Z1 at time T1 by the control section 10. Z0 is a position where the movable section 22C is not driven and the Peltier elements 21C and 21D are not in contact with the user U, as shown in (A) of FIG. 9(A). Z1 is a position where the movable section 22C is driven and the Peltier elements 21C and 21D are closest to the user U in the Z axis direction, as shown in (B) of FIG. 9.

As shown in (B) of FIG. 10, if the second control signal is generated by the control section 10 at time T0, the Peltier element 21C increases the temperature from C0 to C1. The temperature C1 is, for example, about 2° C. higher than the temperature of the skin of the user U, and for example, is 37° C. This is a preliminary heating to present the thermal sensation.

Next, if the first control signal is generated by the control section 10 at time T1, the temperature is further increased from C1 to C2. Then, the Peltier element 21C is moved outside of the space W by the movable section 22C to present the thermal sensation to the user U. Here, the temperature of C2 is, for example, 39° C.

As shown in (C) of FIG. 10, if the second control signal is generated by the control section 10 at time T0, the Peltier element 21D decreases the temperature from C0 to C3. The temperature C3 is, for example, about 2° C. lower than the temperature of the skin of the user U, and for example, is 33° C. This is a preliminary cooling to present the thermal sensation.

Next, if the first control signal is generated by the control section 10 at time T1, the temperature is further decreased from C3 to C4. Then, the Peltier element 21D is moved outside of the space W by the movable section 22C to present the thermal sensation to the user U. Here the temperature of C4 is, for example, 26° C.

This allows the thermal sensation to be presented to the user U at the appropriate timing. Since the Peltier elements 21C and 21D are held in the Z0 position until the above timing, the heat generated by the Peltier elements 21C and 21D is suppressed from being released to the user U side, which is outside of the space W. By moving the movable section 22C by the control section 10 at the above timing, the heat generated by heating or cooling the Peltier elements 21C and 21D to the predetermined temperature is transferred to the user U side. Therefore, the heat is transferred to the user U at once, making it easier for the user U to perceive the thermal sensation. Here, in this embodiment, the movable section 22C makes the Peltier elements 21C and 21D protrude outside of the opening surface 201C (outside of space W), but it is not limited to moving them to the outside of the space W. For example, a case in which they are moved to a positive direction side of the Z-axis within the space W, which is inside the opening surface 201C (in negative direction of Z-axis), is also included. In other words, the movable section 22C needs only be configured to move the Peltier elements 21C and 21D within the space W toward the outside of the space W.

In this embodiment, the movable section 22C is the cam mechanism, but it is not limited to this, and may be a pump. The Peltier elements 21C and 21D are in direct contact with the user U, but this is not limited to this. A metallic plate such as copper may be placed on the Peltier elements 21C and 21D and the thermal sensation may be presented to the user U via the metallic plate.

In this embodiment, the warm/cool source unit 20C is installed on the wrist, but it should be appreciated that it is not limited to this, and the warm/cool source unit 20C may be installed on the ankle, the neck, the torso, the head, etc., or on a gripping part of a game controller. Also, for example, a plurality of warm/cool source units 20C may be attached to a back of the neck or arms to provide a gradation in the thermal sensation provided to the user U.

In this embodiment, the thermal sensation is presented to the user U only by the temperature control, but it should be appreciated that it is not limited to this, and it may have a tactile sensation presentation section that presents other tactile sensation sensations such as vibration or pressure. For example, a vibration device may be attached to the Peltier elements 21C and 21D to provide vibration to the user U by the control section 10 in accordance with the timing of the thermal sensation presentation (timing when first control signal is generated). This allows a stronger presentation of the thermal sensation to the user U.

Modified Example 2-1

Figure 11:
FIG. 11 A modified example of the second embodiment regarding a contact surface between the Peltier element and the user, (A) shows a stick grasped by the user, (B) shows the Peltier element including heat sinks, and (C) shows the heat sink being inserted into a hole in the stick.
Figure 11:
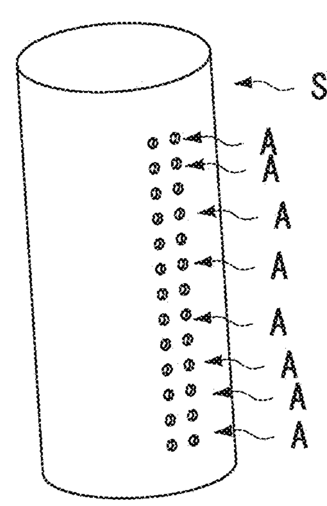
Figure 11:
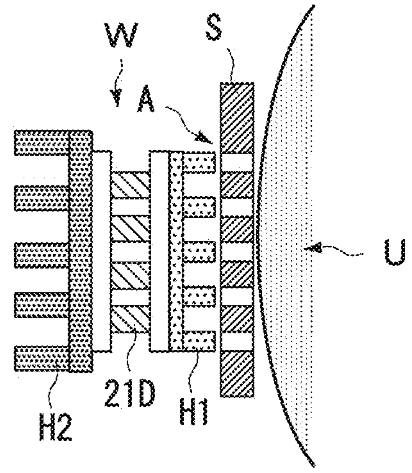
Figure 11:
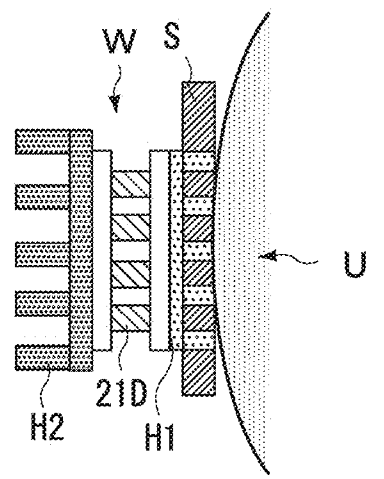

FIG. 11 shows a modified example of the second embodiment regarding a contact surface between the Peltier element 21D and the user U. (A) shows a stick S grasped by the user U, (B) shows the Peltier element 21D including heat sinks H1 and H2, (C) shows the heat sink H1 being inserted into holes A in the stick S. Hereinafter, the configuration that differs from the second embodiment will be mainly described, and the configuration similar to the configuration of the second embodiment will be marked with the same symbols and its description will be omitted or simplified.

This modified example differs from the second embodiment in that the heat sinks H1 and H2 are attached to the Peltier element 21D. The Peltier element 21D has the heat sink H1 for heat absorption attached to the user U side and the heat sink H2 for heat dissipation attached to the opposite side of the heat sink H1, and is accommodated in the space W in the stick S. The heat sink H1 for heat absorption has a projection large enough to penetrate the holes A in the stick S. As shown (C) of FIG. 11, the heat sink H1 is inserted into the holes A when presenting the thermal sensation to the user U, and the thermal sensation is presented to the user U through the heat sink H1.

In this modified example, the Peltier element is for cooling, but it should be appreciated that it is not limited to this, and the Peltier element may be for heating. A method of moving the Peltier element 21D is not limited, but is similar to the second embodiment, for example.

Modified Example 2-2

Figure 12:
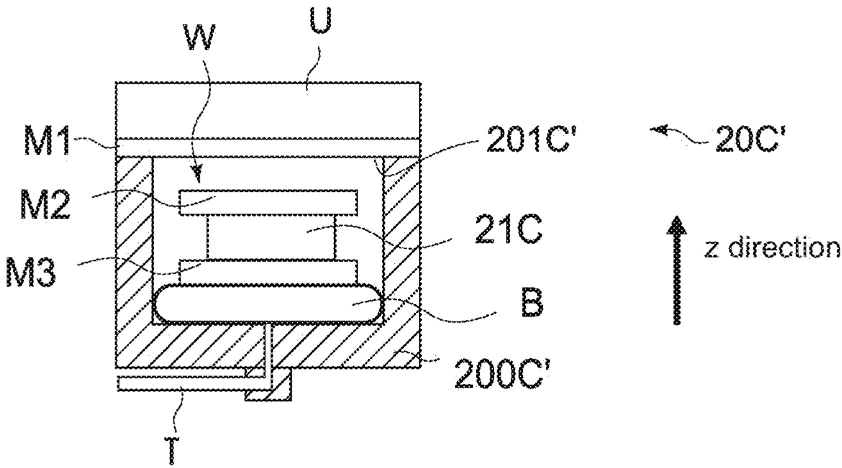
FIG. 12 A diagram showing presentation of the thermal sensation to the user through copper plates, (A) shows a state in which the Peltier element is not in contact with the copper plate, which is in contact with the user, and (B) shows a state in which the copper plate is in contact with the Peltier element, which is in contact with the user.
Figure 12:
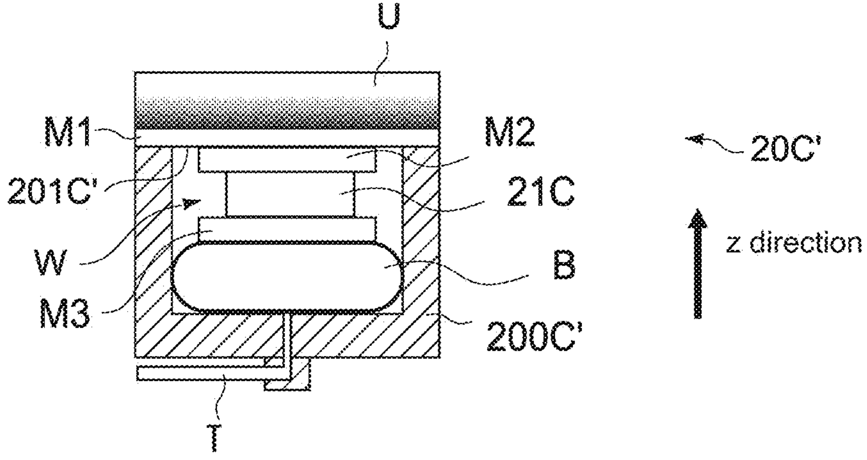

FIG. 12 shows a diagram showing the presentation of the thermal sensation to the user U through the copper plates M1 and M2. (A) shows a state in which the Peltier element 21C for heating is not in contact with the copper plate M1, which is in contact with the user U, and (B) shows a state in which the copper plate M1 is in contact with the Peltier element 21C, which is in contact with the user U. Hereinafter, the configuration that differs from the second embodiment will be mainly described, and the configuration similar to the configuration of the second embodiment will be marked with the same symbols and its description will be omitted or simplified.

This modified example differs from the second embodiment in that the copper plate M1 is provided between the user U and the Peltier element 21C. In this modified example, a warm/cool source unit 20C' has the Peltier element 21C, an enclosure 200C' having a space W for accommodating the Peltier element 21C, a balloon B, and a tube T. The copper plate M1 is provided on an opening surface 201C' of the enclosure 200C', and the copper plate M1 is provided on the contact surface between the user U and the enclosure 200C'. The Peltier element 21C has the copper plate M2 provided on a copper plate M1 side and a copper plate M3 for heat dissipation provided on an opposite side of the copper plate M2.

The balloon B is provided between the copper plate M3 and the enclosure 200C', and expands in the Z-axis direction when air flows in and contracts when air is discharged. The tube T also forms a path for air to flow into and out of the balloon B from a pump (not shown).

Figure 13:
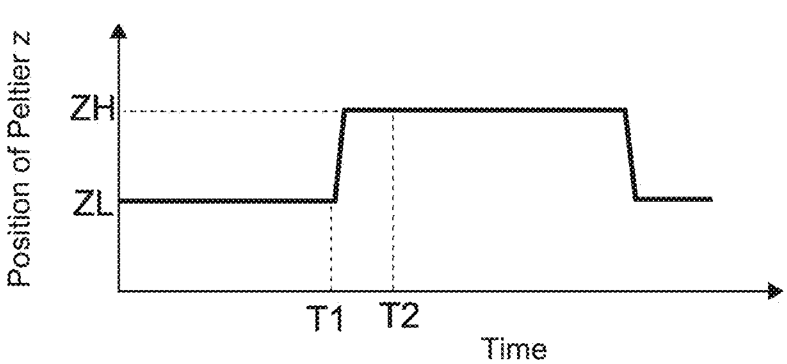
FIG. 13 A diagram showing the temperature control of the Peltier element based on the position of the Peltier element, (A) shows the position of the Peltier element, (B) shows the temperature of the copper plate in contact with the user, and (C) shows the temperature of the copper plate on the Peltier element.
Figure 13:
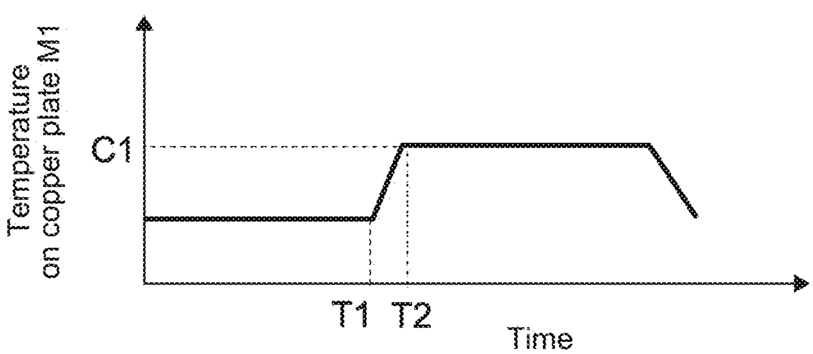
Figure 13:
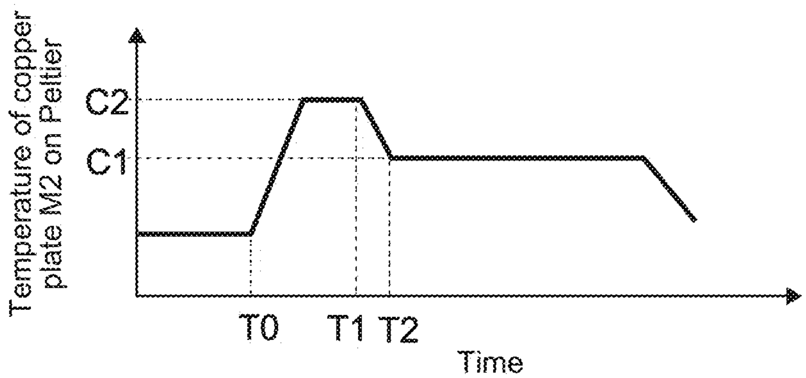

FIG. 13 is a diagram showing the temperature control of the Peltier element 21C based on the position of the Peltier element 21C. (A) shows the position of the Peltier element 21C, (B) shows the temperature of the copper plate M1 in contact with the user U, and (C) shows the temperature of the copper plate M2 on the Peltier element 21C.

As shown in (C) of FIG. 13, time TO is the timing when the second control signal is generated by the control section 10. The temperature is increased to temperature C2 at the timing of time TO. The temperature C2 is a temperature higher than the temperature C1 on the copper plate M1, which corresponds to the predetermined thermal sensation to be presented to the user U.

Next, at time T1, which is earlier than T2, the timing for presenting the predetermined thermal sensation to the user U, the first control signal is generated and air flows into the balloon B to bring copper plate M2 into contact with copper plate M1. At time T1, the temperature on the copper plate M2 is C2, but the temperature is cooled to C1 by contact with the copper plate M1, allowing the user U to present the predetermined thermal sensation.

In this modified example, in a case where the predetermined thermal sensation is presented to the user U, it is necessary to increase the temperature of the copper plate M1 to a temperature higher than that corresponding to the predetermined thermal sensation. In this case, even if the copper plate M1 comes into contact with the copper plate M2, the copper plate M1 cannot immediately reach the predetermined temperature C1. Therefore, by bringing the copper plate M2 into contact with copper plate M1 at the timing earlier than T2, the user U can be presented with the predetermined thermal sensation at the appropriate timing. In addition, by blocking the opening surface 201C' with the copper plate M1, a waterproof property can be improved.

In this modified example, the Peltier element is for heating, but it may be the Peltier element for cooling. In addition, it is not limited to the mechanism to raise and lower the Peltier element by expanding and contracting the balloon B using the pump, but the Peltier element may be raised and lowered by a motor or the like. In this modified example, the copper plate is used, but it is not limited to this, and other metals or alloys such as aluminum may also be used.

Modified Example 2-3

Figure 14:
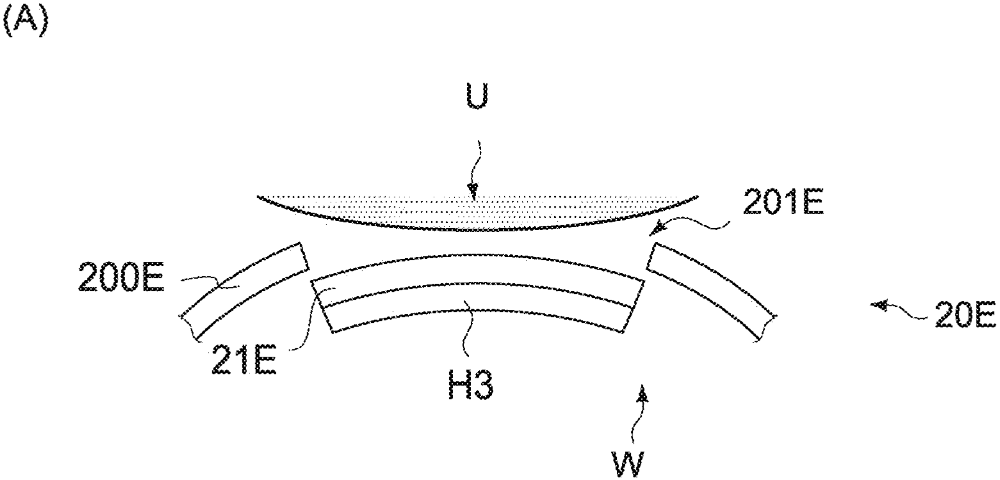
FIG. 14 A modified example regarding a contact mechanism between a Peltier element and the user, (A) shows a state in which the user and the Peltier element are not in contact, and (B) shows a state in which the user and the Peltier element are in contact.
Figure 14:
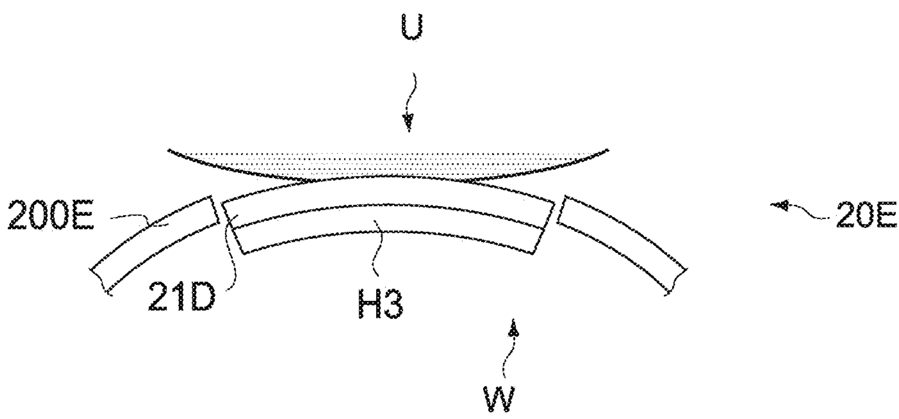
Figure 15:
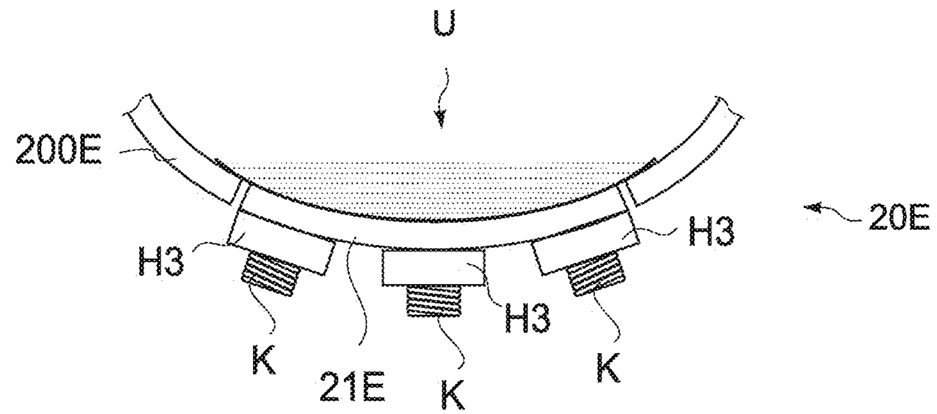
FIG. 15 A diagram regarding an elevation mechanism of the Peltier element, (A) shows that the elevation mechanism is a spring, and (B) shows that the elevation mechanism is a balloon.
Figure 15:
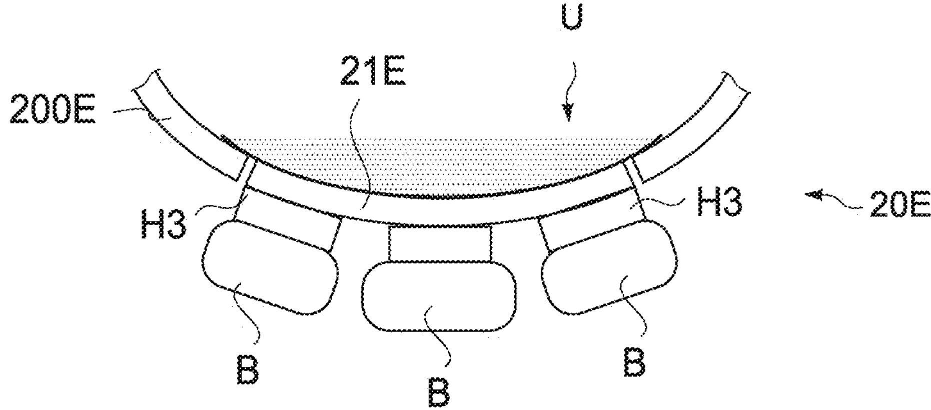

FIG. 14 is a modified example regarding a contact mechanism between a Peltier element 21E and the user U. (A) shows a state in which the user U and the Peltier element 21E are not in contact, and (B) shows a state in which the user U and the Peltier element 21E are in contact. FIG. 15 is a diagram regarding an elevation mechanism of the Peltier element 21E. (A) shows that the elevation mechanism is springs K, and (B) shows that the elevation mechanism is the balloons B. Hereinafter, the configuration that differs from the second embodiment will be mainly described, and the configuration similar to the configuration of the second embodiment will be marked with the same symbols and its description will be omitted or simplified.

This modified example differs from the second embodiment in that the Peltier element 21E is a flexible Peltier element. In this modified example, a warm/cool source unit 20E has a space W to accommodate the Peltier element 21E, and includes a curved-shaped enclosure 200E including a curved-shaped opening surface 201E, the Peltier element 21E, which is a flexible Peltier element that is shaped along the curved surface and faces the opening surface 201E, and a heat sink H3 that is in contact with a surface of the Peltier element 21E at an opposite side of the user U side. The Peltier element 21E is a Peltier element formed, for example, of a Bi—Te based semiconductor and silicon resin. As shown in (A) and (B) of FIG. 14, it is not especially limited to the mechanism for raising and lowering the Peltier element 21E to penetrate the opening surface 201E, and there are, for example, a motor (VCM (Voice Coil Motor), ultrasonic motor), the balloon, a solenoid, etc. The control related to heating and cooling of the Peltier element 21E is similar to that in the second embodiment and is therefore omitted.

The above configuration enables the predetermined thermal sensation to be presented to the user U, even if a part to present the thermal sensation to the user U is a convex curved surface.

In this modified example, the Peltier element 21E is not limited to heating or cooling. Also, the part that presents the thermal sensation to the user U is not limited to the convex curved surface, but may be concave. With respect to the elevation mechanism of the Peltier element 21E described above, as shown in (A) and (B) of FIG. 15, a plurality of springs K and balloons B may be used to present the predetermined thermal sensation to the user U. This makes it possible, for example, to control the center spring K of the three springs K to be pressed more strongly than the other springs K, etc., thereby presenting a more appropriate thermal sensation to the user U.

Modified Example 2-4

Figure 16:
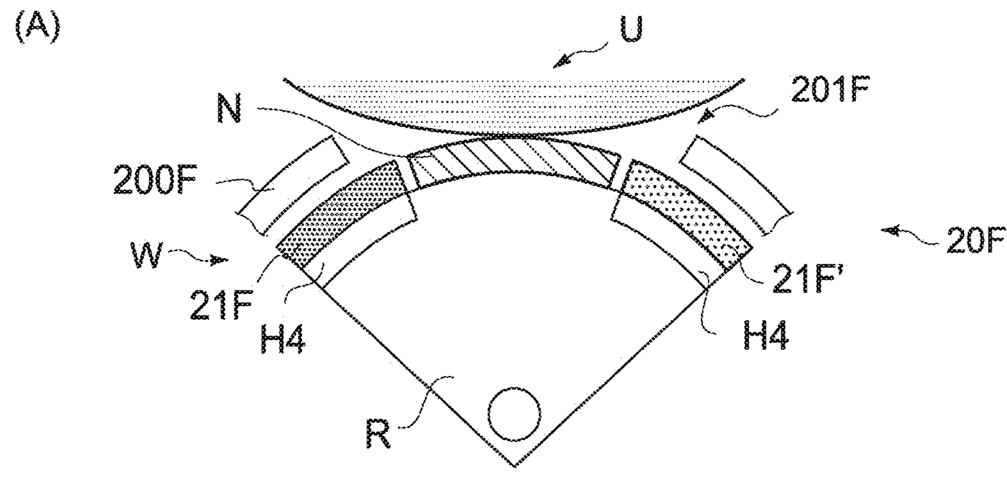
FIG. 16 A modified example of the contact mechanism between Peltier elements and the user, (A) shows a state in which the user and the Peltier elements are not in contact, (B) shows a state in which the user and the Peltier element for cooling are in contact by a rotation mechanism, and (C) shows a state in which the user and the Peltier element for heating are in contact by the rotation mechanism.
Figure 16:
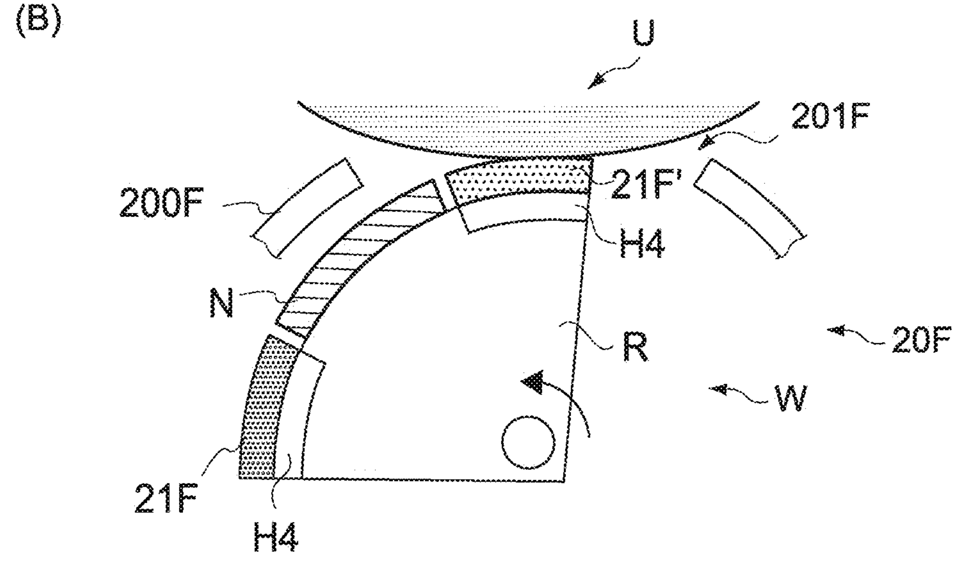
Figure 16:
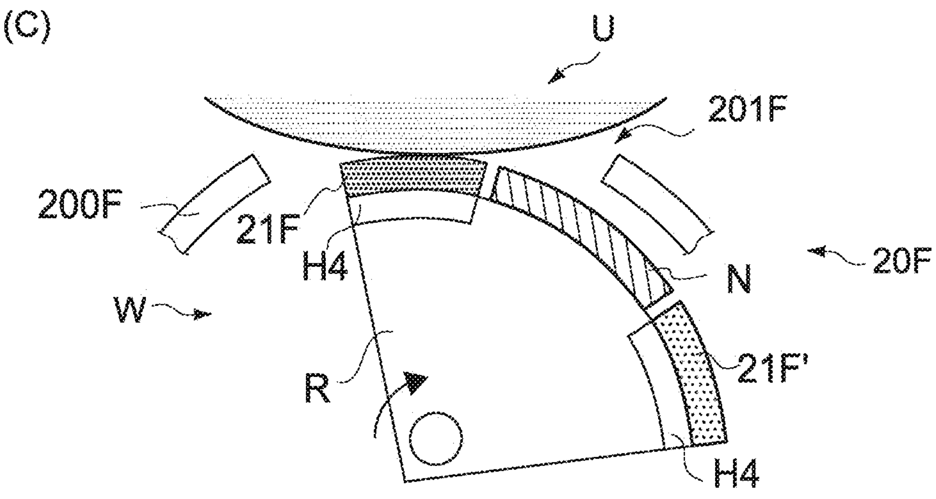

FIG. 16 shows a modified example of a contact mechanism between Peltier elements 21F, 21F' and the user U. (A) shows a state in which the user U and the Peltier elements 21F, 21F' are not in contact, (B) shows a state in which the user U and the Peltier element 21F' for cooling are in contact by a rotation mechanism R, and (C) shows a state in which the user U and the Peltier element 21F for heating are in contact by the rotation mechanism R. Hereinafter, the configuration that differs from the second embodiment will be mainly described, and the configuration similar to the configuration of the second embodiment will be marked with the same symbols and its description will be omitted or simplified.

This modified example differs from the second embodiment in that the thermal sensation provided to the user U is switched by the rotation mechanism R. In this modified example, a warm/cool source unit 20F has the Peltier element 21F for heating, the Peltier element 21F' for cooling, an enclosure 200F having the space W that accommodates the Peltier element 21F and the Peltier element 21F' and including a curved-shaped opening surface 201F, heat sinks H4 in contact with surfaces of the Peltier element 21F and the Peltier element 21F' at an opposite side of the user U side, an intermediate layer N disposed between the Peltier element 21F and the Peltier element 21F', and the rotation mechanism R that allows rotation of the Peltier elements 21F, 21F', the heat sink H4, and the intermediate layer N.

As shown in (A) to (C) of FIG. 16, the rotation mechanism R is configured to be fan-shaped and rotatable along the shape of the opening surface 201F. The intermediate layer N is configured of, for example, rubber or metal, and is in contact with the user U when the user U is not being presented with the thermal sensation, as shown in (A) of FIG. 16.

As shown in (B) of FIG. 16, if the thermal sensation (coldness) is presented to the user U, the rotation mechanism R is rotated to bring the Peltier element 21F' into contact with the user U. As shown in (C) of FIG. 16, if the thermal sensation (warmth) is presented to the user U, the rotation mechanism R is rotated to bring the Peltier element 21F into contact with the user U.

Thus, by bringing the Peltier elements 21F, 21F', which are heated or cooled to the predetermined temperature from the intermediate layer N, into contact with the user U, the predetermined thermal sensation can be presented to the user U with at an appropriate time.

In this modified example, the flexible Peltier elements 21F and 21F' are in contact with the user U, but it should be appreciated that it is not limited to this, and for example, a curved-shaped metal plate (such as copper or aluminum) may be formed on a flat-shaped Peltier element.

Application Examples

In the present technology example, the detection section 30 detects the position and movement of the user U and presents the thermal sensation to the user U based on the detection result, but it is not limited to this. In a case where information (scene condition) about what kind of thermal sensation is presented in certain scene in a movie, for example, can be acquired in advance, the information is acquired by the acquisition section 11 and stored in a storage section (not shown). Then, based on the data stored in the storage section, the control section 10 may present the thermal sensation to the user U in accordance with the timing when a character in the movie shows a technique while watching the movie.

Figure 17:
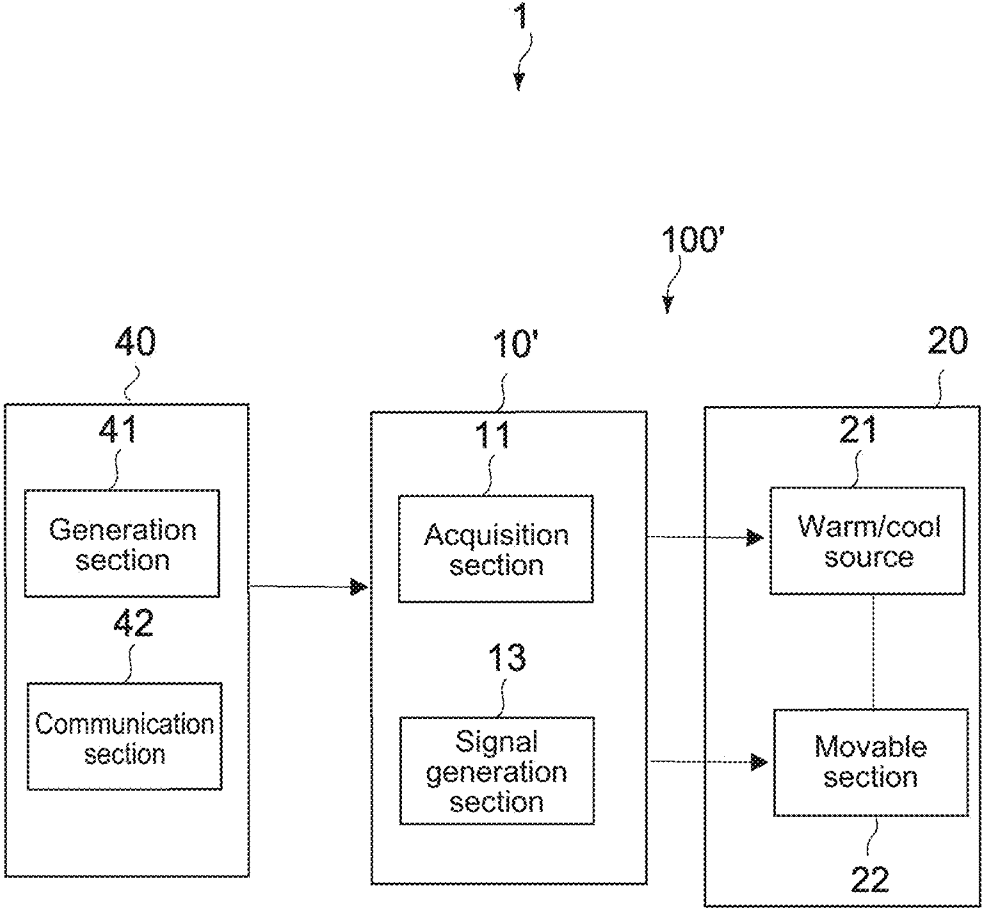
FIG. 17 A block diagram showing a configuration of a thermal sensation presentation system including an external apparatus and a thermal sensation presentation apparatus.

FIG. 17 is a block diagram showing a configuration of a thermal sensation presentation system 1 including an external apparatus 40 and a thermal sensation presentation apparatus 100'.

As shown in FIG. 17, the thermal sensation presentation apparatus 100' may present the thermal sensation to the user U based on the information to present the thermal sensation transmitted from an external source. The thermal sensation presentation system 1 has the external apparatus 40 and the thermal sensation presentation apparatus 100. The external apparatus 40 has a generation section 41 that generates information for presenting the thermal sensation to the user U and a communication section 42 that transmits the information generated by the generation section 41.

A control section 10' has the acquisition section 11 and the signal generation section 13. The acquisition section 11 acquires information (scene condition) transmitted by the communication section 42. The signal generation section 13 generates the second control signal to heat or cool the warm/cool source 21 to the predetermined temperature before generating the first control signal to drive the movable section 22 based on the information acquired by the acquisition section 11.

Here, it describes a case in which the external apparatus 40 is a home video game machine and the warm/cool source 21 is in the gripping part of a controller of the game machine. If the user is playing the home video game machine and the user presses a button A in the next action to throw flames to a character in the game (virtual space), the generation section 41 generates information that the user may throw flames to the character in the game. The communication section 42 transmits the information to the control section 10'. The acquisition section 11 acquires the information transmitted by communication section 42. The signal generation section 13 allows the warm/cool source 21 to be heated to the predetermined temperature based on the information acquired by the acquisition section 11. When the acquisition section 11 next acquires the information from the external apparatus 40 that the user presses the button A, the signal generation section 13 controls the warm/cool source 21 so that the gripping part of the controller becomes hot. In addition to the home video game machine, it can be applied, for example, to a VR (Virtual Reality) and an AR (Augmented Reality). As an example, when a user wearing a VR goggle faces a specific direction in a virtual space, a thermal sensation may be presented by the warm/cool source unit 20 as shown in (A) and (B) of FIG. 7. Here, the virtual space is not limited to a game screen or a VR space as an example, but can be any space that is different from the real space, which is a spatial coordinate in which the user exists.

The above-mentioned scene condition is a condition for presenting the thermal sensation input from the external apparatus 40, and includes a condition such as: a condition for when to provide a hot air to the user as in a movie, a condition for what operation makes the controller hot as in the game, and a condition for what kind of thermal sensation is presented based on the position or the movement of the user in the virtual space (game screen, VR space, AR space, etc.). It should be appreciated that it is not limited to input the scene condition by the external apparatus 40, but by any apparatus that provides the condition for presenting the thermal sensation such as the detection section 30. The condition may be such that: what kind of thermal sensation is presented based on the position or the movement of the user in the real space input by the detection section 30.

Each configuration of the thermal sensation presentation system, the thermal sensation presentation apparatus, the warm/cool source unit, the warm/cool source, etc. described above with reference to the respective drawings is only one embodiment, and may be arbitrarily modified to the extent not to depart from the intent of the present technology. That is, any other configuration may be adopted to implement the present technology.

The present technology may also have the following structures.

(1) A thermal sensation presentation apparatus, including:
a warm/cool source,
an enclosure having a space to accommodate the warm/cool source,
a movable section that moves heat generated by heating or cooling the warm/cool source to a predetermined temperature from the space to outside of the space,
a control section that generates a second control signal to heat or cool the warm/cool source to the predetermined temperature before generating a first control signal to drive the movable section.

(2) The thermal sensation presentation apparatus according to (1), in which
the control section generates the first control signal and the second control signal based on a scene condition.

(3) The thermal sensation presentation apparatus according to (1) or (2), in which
the control section generates the first control signal and the second control signal based on a position or a movement of the user in a real space or a virtual space.

(4) The thermal sensation presentation apparatus according to any one of (1) to (3), in which
the enclosure has an opening surface that connects the space to the outside of the space, and
the movable section is a shutter that can open and close the opening surface, and blocks the heat from moving out of the space in a closed state.

(5) The thermal sensation presentation apparatus according to any one of (1) to (3), in which
the movable section is configured to support the warm/cool source and allow the warm/cool source to move toward the outside of the space.

(6) The thermal sensation presentation apparatus according to (5), in which
the enclosure has an opening surface that connects the space to the outside of the space, and
the movable section is configured to allow the warm/cool source to move from the space to the outside of the space through the opening surface.

(7) The thermal sensation presentation apparatus according to any one of (1) to (6), further including:
a tactile sensation presentation section that presents vibration or pressure, in which
the control section controls the tactile sensation presentation section when generating the first control signal.

(8) The thermal sensation presentation apparatus according to (4), in which
the warm/cool source is an infrared heater or a cooling fan.

(9) The thermal sensation presentation apparatus according to (5) or (6), in which
the warm/cool source is a resistance heater or a Peltier element.

(10) The thermal sensation presentation apparatus according to (1), further including:
a detection section that detects surroundings of the warm/cool source, in which
the control section generates the first control signal and the second control signal based on a detection result of the detection section.

(11) The thermal sensation presentation apparatus according to (10), in which
the detection section detects a position or a movement of the user who exists around the warm/cool source, and
the control section generates the first control signal and the second control signal based on the position or the movement of the user.

(12) A thermal sensation presentation system, including:
a generation section that generates information for presenting a thermal sensation to a user,
a communication section that transmits the information generated by the generation section,
a warm/cool source,
an enclosure having a space to accommodate the warm/cool source,
a movable section that moves heat generated by heating or cooling the warm/cool source to a predetermined temperature from the space to outside of the space,
a control section that acquires the information transmitted by the communication section and, based on the acquired information, generates a second control signal to heat or cool the warm/cool source to a predetermined temperature before generating a first control signal to drive the movable section.

(13) The thermal sensation presentation system according to (12), in which
the control section generates the first control signal and the second control signal based on a scene condition.

(14) The thermal sensation presentation system according to (12) or (13), in which
the control section generates the first control signal and the second control signal based on a position or a movement of the user in a real space or a virtual space.

(15) The thermal sensation presentation system according to any one of (12) to (14), in which the enclosure has an opening surface that connects the space to outside of the space, the movable section is a shutter that can open and close the opening surface, and blocks the heat from moving out of the space in a closed state.

(16) The thermal sensation presentation system according to any one of (12) to (15), in which the movable section is configured to support the warm/cool source and allow the warm/cool source to move toward the outside of the space.

(17) The thermal sensation presentation system according to (15), in which the enclosure has an opening surface that connects the space to the outside of the space, the movable section is configured to allow the warm/cool source to move from the space to the outside of the space through the opening surface.

(18) The thermal sensation presentation system according to any one of (12) to (17), further including:

a tactile sensation presentation section that presents vibration or pressure, in which the control section controls the tactile sensation presentation section when generating the first control signal.

(19) The thermal sensation presentation system according to (12), further including:

a detection section that detects surroundings of the warm/cool source, in which the control section generates the first control signal and the second control signal based on a detection result of the detection section.

(20) The thermal sensation presentation system according to (19), in which the detection section detects a position or a movement of the user who exists around the warm/cool source, and the control section generates the first control signal and the second control signal based on the position or the movement of the user.

(21) The thermal sensation presentation system according to (15), in which the warm/cool source is an infrared heater or a cooling fan.

(22) The thermal sensation presentation system according to (15) or (16), in which the warm/cool source is a resistance heater or a Peltier element.

REFERENCE SIGNS LIST

1 thermal sensation presentation system
10 control section
11 acquisition section
12 determination section
13 signal generation section
20 warm/cool source unit
21 warm/cool source
22 movable section
30 detection section
40 external apparatus
100 thermal sensation presentation apparatus
200 enclosure
201 opening surface
U user
W space

The invention claimed is:

1. A thermal sensation presentation apparatus, comprising:

a warm/cool source, an enclosure having a space to accommodate the warm/cool source, a movable section movable between a first state in which the warm/cool source is thermally isolated within the space from a user and a second state that moves heat generated by heating or cooling the warm/cool source to a predetermined temperature from the space to outside of the space towards the user, a control circuit configured to generate a second control signal to heat or cool the warm/cool source to the predetermined temperature in response to a detected approach of the user in a real space or a virtual space toward a target position, while the movable section is in the first state, and, in response to the user reaching the target position or a scene in a video, generate a first control signal to drive the movable section to be in the second state after generating the second control signal.

2. The thermal sensation presentation apparatus according to claim 1, wherein the control circuit configured to generate the first control signal and the second control signal based on a scene condition.

3. The thermal sensation presentation apparatus according to claim 1, wherein the enclosure has an opening surface that connects the space to the outside of the space, and the movable section is a shutter that can open and close the opening surface, and blocks the heat from moving out of the space in a closed state.

4. The thermal sensation presentation apparatus according to claim 1, wherein the movable section is configured to support the warm/cool source and allow the warm/cool source to move toward the outside of the space.

5. The thermal sensation presentation apparatus according to claim 4, wherein the enclosure has an opening surface that connects the space to the outside of the space, and the movable section is configured to allow the warm/cool source to move from the space to the outside of the space through the opening surface.

6. The thermal sensation presentation apparatus according to claim 1, further comprising:

a tactile sensation presentation section that presents vibration or pressure, wherein the control circuit is configured to control the tactile sensation presentation section when generating the first control signal.

7. The thermal sensation presentation apparatus according to claim 3, wherein the warm/cool source is an infrared heater or a cooling fan.

8. The thermal sensation presentation apparatus according to claim 4, wherein the warm/cool source is a resistance heater or a Peltier element.

9. The thermal sensation presentation apparatus according to claim 1, further comprising:

a detector configured to detect surroundings of the warm/cool source, wherein the control circuit is configured to generate the first control signal and the second control signal based on a detection result of the detector.

10. The thermal sensation presentation apparatus according to claim 9, wherein the detector is configured to detect a position or a movement of the user who exists around the warm/cool source, and the control circuit is configured to generate the first control signal and the second control signal based on the position or the movement of the user.

11. A thermal sensation presentation system, comprising:

a generation circuit configured to generate information for presenting a thermal sensation to a user and transmit the information generated, a warm/cool source, an enclosure having a space to accommodate the warm/cool source, a movable section movable between a first state in which the warm/cool source is thermally isolated within the space from a user and a second state that moves heat generated by heating or cooling the warm/cool source to a predetermined temperature from the space to outside of the space towards the user, a control circuit configured to:

acquire the information transmitted by the generation circuit and, based on the acquired information, generate a second control signal to heat or cool the warm/cool source to a predetermined temperature in response to a detected approach of the user in a real space or a virtual space toward a target position, while the movable section is in the first state, and, in response to the user reaching the target position or a scene in a video, generate a first control signal to drive the movable section to be in the second state after generating the second control signal.

12. The thermal sensation presentation system according to claim 11, wherein the control circuit is configured to generate the first control signal and the second control signal based on a scene condition.

13. The thermal sensation presentation system according to claim 11, wherein the enclosure has an opening surface that connects the space to outside of the space, the movable section is a shutter that can open and close the opening surface, and blocks the heat from moving out of the space in a closed state.

14. The thermal sensation presentation system according to claim 11, wherein the movable section is configured to support the warm/cool source and allow the warm/cool source to move toward the outside of the space.

15. The thermal sensation presentation system according to claim 13, wherein the enclosure has an opening surface that connects the space to the outside of the space, the movable section is configured to allow the warm/cool source to move from the space to the outside of the space through the opening surface.

16. The thermal sensation presentation system according to claim 11, further comprising:

a tactile sensation presentation section that presents vibration or pressure, wherein the control circuit is configured to control the tactile sensation presentation section when generating the first control signal.

17. The thermal sensation presentation system according to claim 11, further comprising:

a detector configured to detect surroundings of the warm/cool source, wherein the control circuit is configured to generate the first control signal and the second control signal based on a detection result of the detector.

18. The thermal sensation presentation system according to claim 17, wherein the detector is configured to detect a position or a movement of the user who exists around the warm/cool source, and the control circuit is configured to generate the first control signal and the second control signal based on the position or the movement of the user.

19. The thermal sensation presentation apparatus according to claim 1, wherein the control circuit is configured to generate the second control signal based on a speed of the approach of the user toward the target position.

20. The thermal sensation presentation apparatus according to claim 9, wherein the detector is further configured to detect a position or movement of an object held by the user, and the control circuit is configured to generate the first control signal and the second control signal based on the position or movement of the object.

* * * * *